US009505710B2

(12) United States Patent
Johnson et al.

(10) Patent No.: US 9,505,710 B2
(45) Date of Patent: Nov. 29, 2016

(54) HYDROXAMIC ACIDS AND USES THEREOF

(71) Applicant: HAWAII BIOTECH, INC., Aiea, HI (US)

(72) Inventors: Alan Thomas Johnson, Kaneohe, HI (US); Seong Jin Kim, Honolulu, HI (US); Sean O'Malley, Honolulu, HI (US); Henry Lee Jackson, Pearl City, HI (US)

(73) Assignee: HAWAII BIOTECH, INC., Honolulu, HI (US)

( * ) Notice: Subject to any disclaimer, the term of this patent is extended or adjusted under 35 U.S.C. 154(b) by 0 days.

(21) Appl. No.: 15/099,438

(22) Filed: Apr. 14, 2016

(65) Prior Publication Data

US 2016/0304443 A1 Oct. 20, 2016

Related U.S. Application Data

(60) Provisional application No. 62/148,442, filed on Apr. 16, 2015.

(51) Int. Cl.

| | |
|---|---|
| ***C07C 259/06*** | (2006.01) |
| ***C07D 213/56*** | (2006.01) |
| ***C07D 295/16*** | (2006.01) |
| ***C07C 259/10*** | (2006.01) |
| ***C07D 207/337*** | (2006.01) |
| ***C07D 239/26*** | (2006.01) |
| ***C07D 239/42*** | (2006.01) |
| ***C07D 231/12*** | (2006.01) |
| ***C07D 295/185*** | (2006.01) |
| ***C07D 295/155*** | (2006.01) |
| ***C07D 233/64*** | (2006.01) |
| ***C07D 303/46*** | (2006.01) |
| ***C07D 211/34*** | (2006.01) |

(52) U.S. Cl.

CPC ........... *C07C 259/06* (2013.01); *C07C 259/10* (2013.01); *C07D 207/337* (2013.01); *C07D 211/34* (2013.01); *C07D 213/56* (2013.01); *C07D 231/12* (2013.01); *C07D 233/64* (2013.01); *C07D 239/26* (2013.01); *C07D 239/42* (2013.01); *C07D 295/155* (2013.01); *C07D 295/16* (2013.01); *C07D 295/185* (2013.01); *C07D 303/46* (2013.01); *C07C 2101/02* (2013.01)

(58) Field of Classification Search

None

See application file for complete search history.

(56) References Cited

U.S. PATENT DOCUMENTS 7,807,720 B2 10/2010 Johnson et al.
7,879,911 B2 2/2011 Johnson et al.
8,119,692 B2 2/2012 Johnson et al.
8,242,174 B2 8/2012 Johnson et al.
2010/0260778 A1 10/2010 Pang et al.

FOREIGN PATENT DOCUMENTS

WO 9216200 A1 10/1992
WO 2010136839 A1 12/2010

OTHER PUBLICATIONS

Database Caplus Chemical Abstracts Service, Columbus, Ohio, US; Database Accession No. 1983:405478, Abstract of El-Kholy, Journal of Heterocyclic Chemistry (1982), 19(6), 1329-34.*

Bornpiani et al. (2016) ACS Combinatorial Science DOI: 10.1021/acscombsci.6b00033.

Silhar et al. Journal of Medicinal Chemistry 56(20):7870-7879, 2013.

O'Malley et al. Bioorg. & Med. Chem. Lett. 23(9):2505-2511 (2013).

Eubanks et al. ACS Medicinal Chemistry Letters 1:268-272 (2010).

Solaja et al. J. Med. Chem. 51(15):4388-4391 (2008).

Caglic et al. J. MedChem. 57(3):669-676 (2014).

Li et al., Molecules 16(1): 202-20 (2010).

Park et al. Infect. Immun. 71(3): 1147-54 (2003).

Videnovic, Milica et al., "Second Generation Steroidal 4-Aminoquinolines Are Potent, Dual-Target Inhibitors of the Botulinurn Neurotoxin Serotype A Metalloprotease and P. falciparum Malaria", Journal of Medicinal Chemistry (2014), 57(10), 4134-4153.

Bremer, Paul T. et al., "Benzoquinones as inhibitors of botulinum neurotoxin serotype A", m Bioorganic & Medicinal Chemistry (2014), 22(15), 3971-3981.

Gomez-Jeria, Juan S., "A preliminary formal quantitative structure-activity relationship study of some 1,7-bis-(amino alkyl)diazachrysene derivatives as inhibitors of Botulinumneurotoxin serotype A light chain and three P. falciparum malaria strains", Journal of Computational Methods in Molecular Design (2014), 4(2), 32-44, 13 pp.

(Continued)

*Primary Examiner* — Karl J Puttlitz

(74) *Attorney, Agent, or Firm* — Pillsbury Winthrop Shaw Pittman

(57) ABSTRACT

Compounds of formula I are provided:

I

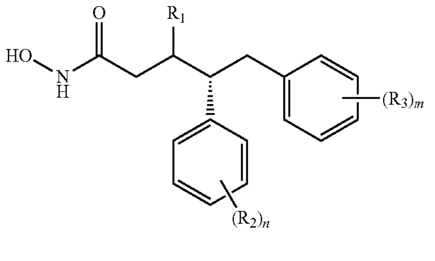

$R_1$ is an alkoxy or $O(CH_2)_pX$, p is an integer from 2 to 3 and X is OH, $NH_2$, or $CO_2H$, m is an integer from 0 to 5, n is an integer from 0 to 5, each $R_2$ is independently selected from hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen, each $R_3$ is independently selected from hydrogen, halogen, alkyl, alkenyl, carboxy, hydroxymethyl, amido, and at least one of $R_2$ and $R_3$ is not hydrogen.

24 Claims, No Drawings

(56) References Cited

OTHER PUBLICATIONS

Gomez-Jeria et al., "Quantum-chemical and docking studies of 8-hydroxy-guinolines as inhibitors of the botulinum neurotoxin a light chain (BoNT/A LC)", Journal of Computational Methods in Molecular Design (2015), 5(2), 25-56.
Guo Jiubiao et al. "Substrate-based inhibitors exhibiting excellent protective and therapeutic effects against Botulinum Neurotoxin A intoxication", Scientific reports (2015), 5, 169.
Burnett et al. J. Med. Chem. 50(9):2127-36(2007).
Nuss et al. ACS Med. Chem. Lett. 1(7) 301-5 (2010).
Capkova et al. Bioorg. Med. Chem. Lett. 20(1):206-8 (2010).
Roxas-Duncan et al. Antimicrob. Agents Chemother. 53(8):3478-3486 (2009).
Opsenica et al. J. Med. Chem. 54(5):1157-69 (2011).
Cardellina II et al. ACS Med. Chem. Lett. 3:387-391 (2012).
Moe et al. Bioorg. Med. Chem. 17(8):3072-9 (2009).
Cai et al. Toxicon. 55(4): 818-826 (2010).
Adler et al. Toxicon 39(2-3):233-43 (2001).
Pang et al. PLoS one 5(4): e10129 (2010).
Silvaggi et al. Chem. Biol. 14:533-542 (2007).
Foran et al. Trends Mol. Med. 9(7): 291-9 (2003).
Stowe et al. Org. Lett. 12(4):756-9 (2010).
Foran et al. J. Biol. Chem. 278(2): 1363-71 (2003).
Capek et al. ACS Chem. Neurosci. 2(6):288-293 (2011).
Burnett et al. Nat. Rev. Drug Disc. 4(4):281-296 (2005).
Amon et al. J. Am. Med. Assoc. 285(8): 1059-1070 (2001).
Dong et al. Proc. Natl. Acad. Sci. U.S.A. 101(41):14701-14706 (2004).
Wein et al. Proc. Natl. Acad. Sci. U.S.A. 102(28):9984-9989 (2005).
Noah et al. Emerg. Med. Clin. North Am. 20(2): 255-71 (2002).
Fernandez-Salas Mov. Discard. 19(8):S23-S34 (2004).
Glik et al. Biosecur. Bioterror. 2(3):216-223 (2004).
Montal Annu. Rev. Biochem. 79:591-617 (2010).
Tsai et al. Proc. Natl. Acad. Sci. U.S.A. 107(38): 16554-16559 (2010).
Cohen et al. Science 294(5542):498-501 (2001).
MacDonald et al. J. Am. Med. Assoc. 253:1275-1278 (1985).
Silhar et al. Bioorg. Med. Chem. Lett. 21:2229-2231 (2011).
Dickerson et al. Curr. Top. Med. Chem. 14: 2094-2102 (2014).
Cardinale et al. Botulinum J. 2(1):16-20 (2011).
Burtea, Alexander et al. "Discovery and SAR study of a sulfonamide hydroxamic acid inhibitor for the botulinum neurotoxin serotype A light chain", MedChemComm (2014), 5(6), 706-710.
Kumar et al. "Recent Developments with Metalloprotease Inhibitor Class of Drug Candidates for Botulinum Neurotoxins", Current Topics in Medicinal Chemistry(2015), 15(7), 685-695.
Poulain et al. The Botulinum J. 1(1):14-87 (2008).
Seki, Hajime et al., "Synthesis/biological evaluation of hydroxamic acids and their prodrugs as inhibitors for Botulinum neurotoxin A light chain", Bioorganic & Medicinal Chemistr, vol. 22, issue3, 1208-1217.
Seki, Hajime et al., "Toward the discovery of dual inhibitors for botulinum neurotoxin A: concomitant targeting of endocytosis and light chain protease activity", Chemical Communications, (2015), 51(28), 6226-6229.
Pubchem, Substance Record for SID 77570624, Create Date: Jun. 12, 2009. [retrieved on Jan. 8-Jun. 24, 2016]. Retrieved from the Internet. <https://pubchem.ncbi.nlm.nih.gov/substance/77570624/version/1/lsection=Top >.entire document.
Jiao, G.-S., et al., Antidotes to Anthrax Lethal Factor Intoxication. Part 1: Discovery of Potent Lethal Factor Inhibitors with in vivo Efficacy. Bioorg. Med. Chem. Lett. (2010), 20:6850-6853.
Kim, S., et al., Antidotes to Anthrax Lethal Factor Intoxication. Part 2: Structural Modifications Leading to Improved In Vivo Efficacy. Bioorg. Med. Chem. Lett. (2011), 21:2030-2033.
Thompson, A. A.; et al. Structural Characterization of Three Novel Hydroxamate-Based Zinc Chelating Inhibitors of the Clostridium botulinum Serotype A Neurotoxin Light Chain Metalloprotease Reveals a Compact Binding Site Resulting from 60/70 Loop Flexibility. Biochem. (2011), 50:4019.
Jiao, G.-S., et al. Antidotes to Anthrax Lethal Factor Intoxication. Part 3: Evaluation of Core Structures and Further Modifications to the C2-side chain. Bioorg. Met Chem. Lett., (2012), 22:2242-2246.
Moayeri, M., et al., Small-Molecule Inhibitors of Lethal Factor Protease Activity Protect against Anthrax Infection. Antimicrob. Agents Chemother (2013), 57:4139.

* cited by examiner

HYDROXAMIC ACIDS AND USES THEREOF

CROSS-REFERENCE TO RELATED APPLICATIONS

This application claims priority to U.S. Provisional Application No. 62/148,442 filed Apr. 16, 2015, the entire contents of which are incorporated herein by reference in its entirety.

STATEMENT OF GOVERNMENT SPONSORSHIP

This invention was made with government support under HDTRA1-13-C-0007 awarded by the Department of Defense, Defense Threat Reduction Agency. The government has certain rights in the invention.

INTRODUCTION

The present disclosure relates to compounds developed to treat exposure to toxins, such as *Botulinum* neurotoxin (BoNT). In particular, the present disclosure relates to hydroxamic acid compounds that serve as inhibitors of toxins, such as BoNT.

*Botulinum* neurotoxin A (BoNT/A), in particular, has an $LD_{50}$ of 1 ng/kg i.v. in mammals (100 ng/kg inhalational, 14 ng/kg oral) (Burnett et al. *Nat. Rev. Drug Disc.* 4(4):281-296 (2005); Wein et al. *Proc. Natl. Acad. Sci. U.S.A.* 102(28): 9984-9989 (2005)). Its ease of production, transport, and delivery make it a significant threat as a biological warfare and bioterrorism weapon (Glik et al. *Biosecur. Bioterror.* 2(3):216-223 (2004). Military programs to develop BoNT as a biological warfare agent in multiple nations have been documented (Arnon et al. *J. Am. Med. Assoc.* 285(8): 1059-1070 (2001); Noah et al. *Emerg. Med. Clin. North Am.* 20(2): 255-71 (2002)). Development and stockpiling of a BoNT inhibitor small molecule therapeutic drug is a priority of the Joint Science and Technology Office-Chemical and Biological Defense/Defense Threat Reduction Agency for warfighter protection. BoNT is a CDC/NIAID Category A Biodefense Pathogen, one of twelve Top Priority Biological Threats for which the Department of Homeland Security has completed full Material Threat Determinations and Population Threat Assessments.

SUMMARY

In some aspects, there are provided compounds of formula I:

I

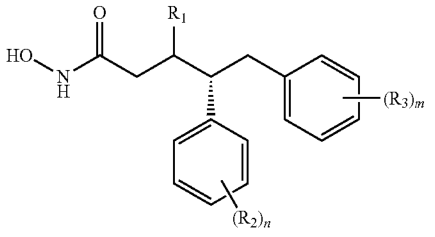

wherein $R_1$ is an alkoxy or $O(CH_2)_pX$;

wherein p is an integer from 2 to 3 and X is OH, $NH_2$, or $CO_2H$;

m is an integer from 0 to 5;

n is an integer from 0 to 5;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen;

each $R_3$ is independently selected from the group consisting of hydrogen, halogen, alkyl, alkenyl, carboxy, hydroxymethyl, amido; and wherein at least one of $R_2$ and $R_3$ is not hydrogen.

In some aspects, there are provided compounds of formula II:

II

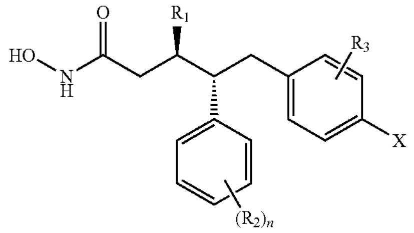

wherein $R_1$ is an alkoxy or $O(CH_2)_pX$;

wherein p is an integer from 2 to 3 and X is OH, $NH_2$, or $CO_2H$;

n is an integer from 0 to 5;

X is a halogen;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen; and $R_3$ is methyl or hydrogen.

In some aspects, there are provided compounds of formula III:

III

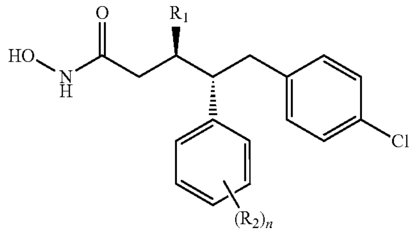

wherein $R_1$ is an alkoxy or $O(CH_2)_pX$;

wherein p is an integer from 2 to 3 and X is OH, $NH_2$, or $CO_2H$;

n is an integer from 0 to 5;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen.

The aforementioned compounds may be formulated in pharmaceutical compositions comprising the compound along with a pharmaceutically acceptable carrier.

The aforementioned compositions may be used in methods of treating a subject exposed to a botulinum toxin comprising administering to the subject the pharmaceutical composition.

DETAILED DESCRIPTION

The botulinum neurotoxins (BoNTs) have been indicated to inhibit acetylcholine release at the neuromuscular junction and other peripheral cholinergic sites (Arnon et al. supra; Poulain et al. *The Botulinum J.* 1(1):14-87 (2008)). At least seven serologically distinct BoNT proteins (types /A through /G) are produced by different strains of the anaerobic bacterium *Clostridium botulinum*; it has been indicated that type /A is the most lethal protein toxin. Symptoms of BoNT intoxication can include difficulty swallowing, impaired vision, muscle weakness, and death due to respiratory failure (MacDonald et al. *J. Am. Med. Assoc.* 253: 1275-1278 (1985)). Exposure to toxin in a bioterrorism scenario could occur through ingestion or inhalation (Park et al. *Infect. Immun.* 71(3): 1147-54 (2003)).

Without being bound by theory, it is postulated that the BoNTs exert their biological effects by a triphasic mechanism involving: 1) serotype-specific 'double-receptor' binding to sialic acid and protein receptors on the surface of motor nerve endings, 2) internalization of the toxin-receptor complex and translocation of proteolytic subunit LC into the cytoplasm, and 3) intraneuronal cleavage of proteins responsible for neurotransmitter release (Montal *Annu. Rev. Biochem.* 79:591-617 (2010)). The holotoxins consists of a heavy chain (HC, MW≈100 kD) that mediates receptor binding and internalization, and a zinc-metalloprotease light chain (LC, MW≈50 kD). The LCs are partially unfolded in the acidic endosome and translocated into the cytosol through a narrow HC channel. They may be phosphorylated and/or palmitoylated once inside the cell; these modifications may enable serotype-specific trafficking that could be responsible for the unique months-long persistence of serotype A (and to a lesser extent, B) (Dong et al. *Proc. Natl. Acad. Sci. U.S.A.* 101(41):14701-14706 (2004); Fernandez-Salas *Mov. Disord.* 19(8):S23-S34 (2004)). While the exact mechanism of persistence has not been fully elucidated, evasion of the ubiquitination-proteasome degradation pathway may be involved (Tsai et al. *Proc. Natl. Acad. Sci. U.S.A.* 107(38): 16554-16559 (2010)).

Light chain /A is believed to exert its intraneuronal effects by site-specific cleavage of SNAP-25 (25 kD synaptosomal associated protein), one of three proteins that form the complex that mediates fusion of carrier vesicles to target membranes (SNARE, soluble N-ethylmaleimide-sensitive fusion protein-attachment protein receptor). Disruption of the SNARE complex can prevent vesicle exocytosis, thus blocking neurotransmitter secretion. Each serotype of BoNT cleaves a SNARE protein at a unique site. The high cleavage specificity of the BoNTs is thought to be due to a complex substrate binding mechanism involving exosites (Montal 2010, supra).

Though there are significant differences in potency among serotypes, with /A being the most potent, a striking difference lies in the persistence of their effect. Recovery of paralyzed nerve endings takes 30-90 days (or more) after intoxication with serotype A, and a few weeks with type B, while the remaining serotypes have a much shorter duration (days or hours) (Adler et al. *Toxicon* 39(2-3):233-43 (2001); Foran et al. *Trends Mol. Med.* 9(7): 291-9 (2003)). Serotype A was selected as the initial target because of its potency and persistence, and also because of its ready availability to potential terrorists and its documented use in large-scale biowarfare production efforts in Iraq in the late 80's (Arnon et al. 2001, supra; Cohen et al. *Science* 294(5542):498-501 (2001)).

The bioterrorism threat is BoNT, a "toxin weapon," rather than the rare natural infection by *C. botulinum*. BoNT is deliverable in cold foods or beverages, or as an aerosol. In a military deployment, aerosolized toxin delivered via bomb, missile, or directly sprayed from a plane would be considered the primary threat; all three delivery mechanisms were explored by the Iraq military before 1991 (Arnon et al. 2001, supra). Homeland Security concerns focus on sabotage in foodstuffs (Wein et al. 2005, supra).

Extracellular interventions are generally ineffective unless given immediately after toxin exposure. Any intervention which targets the initial steps in intoxication (binding, translocation, or endocytosis (Montal 2010, supra)) generally cannot provide benefit to neurons which are already intoxicated by intracellular LC; nor can such an intervention accelerate recovery from paralysis. Importantly, BoNT/A LC reaches its intraneuronal target site within hours after exposure and persists in neurons for months (Montal 2010, supra). Based upon the purported mechanism of action for BoNT, two efficacy profiles are possible for a small molecule intraneuronal LC inhibitor, Type I and Type II, as detailed further below. In some embodiments, a therapeutic provides both types of efficacy.

Type I Efficacy involves slowing or halting progression of intoxication. Type I efficacy results from inhibition of the intraneuronal LC activity before proteolysis of SNAP-25 has reached levels that result in functional failure of exocytosis. The window of opportunity for Type I intervention remains to be fully elucidated, but it is postulated to be significantly longer than the window for protection through systemic clearance of extracellular toxin.

Type II Efficacy involves accelerating recovery of paralyzed tissue. Type II efficacy results from inhibition of LC activity in a neuron which is already functionally incompetent in terms of exocytosis. Under this circumstance, exocytosis may be restored upon attaining functional levels of newly synthesized SNAP-25. Depending on SNAP-25 depletion at initiation of therapy and the rate of SNAP-25 turnover (Foran et al. *J. Biol. Chem.* 278(2): 1363-71 (2003)) restoration of normal function could occur in days with LC inhibitor therapy as opposed to months without it. Type II Efficacy is generally not achieved by any extraneuronal therapy.

An advanced agent may be artificially engineered to bypass existing countermeasures or produce a more severe or otherwise enhanced spectrum of disease. Genetic engineering of an infectious organism vector which could deliver BoNT LC into cells has been studied (Arnon et al. (2001), supra). Such an advanced agent, with BoNT LC delivered in a viral vector such as vaccinia, may be unaffected by any therapeutics acting against the native toxin proteins or its entry mechanism. For defense against such a 'next generation' infectious BoNT LC advanced agent, a countermeasure directly targeting the proteolytic action of BoNT LC may be effective.

Small molecules capable of inhibiting the proteolytic activity of BoNT/A LC have been indicated (Adler et al. (2008), supra; Li et al. *Molecules* 16(1): 202-20 (2010); Dickerson et al. *Curr. Top. Med. Chem.* 14: 2094-2102 (2014)). These include small molecule inhibitors containing a hydroxamic acid zinc binding group (Pang et al. *PLoS one* 5(4): e10129 (2010); Stowe et al. *Org. Lett.* 12(4):756-9 (2010); Capek et al. *ACS Chem. Neurosci.* 2(6):288-293

(2011)). The hydroxamic acid moiety has been shown to bind to the active site zinc in several reported co-crystal structures of inhibitors bound in the active site (Silvaggi et al. *Chem. Biol.* 14:533-542 (2007)).

Other inhibitors include those based on peptides, quinolines (Burnett et al. *J. Med. Chem.* 50(9):2127-36 (2007); Roxas-Duncan et al. *Antimicrob. Agents Chemother.* 53(8): 3478-3486 (2009); Caglic et al. *J. Med. Chem.* 57(3):669-676 (2014)), thiols (Moe et al. *Bioorg. Med. Chem.* 17(8): 3072-9 (2009)), polycationic small molecules (Nuss et al. *ACS Med. Chem. Lett.* 1(7): 301-5 (2010); Opsenica, Burnett et al. *J. Med. Chem.* 54(5):1157-69 (2011)), and other groups (Cai et al. *Toxicon.* 55(4): 818-826 (2010); Capkova et al. *Bioorg. Med. Chem. Lett.* 20(1):206-8 (2010); Cardinale et al. *Botulinum* J. 2(1):16-20 (2011); Silhar et al. *Bioorg. Med. Chem. Lett.* 21:2229-2231 (2011); Cardellina II et al. *ACS Med. Chem. Lett.* 3:387-391 (2012)).

Drugs containing a hydroxamic acid zinc-binding moiety have been approved for use by the FDA. The following small molecules bearing hydroxamic acids have received FDA approval for use in humans: Verinostat (Zolinza), Belinostat (Beleodaq), Deferoxamine (Desferal), Bufexamac (Paraderm), and Panobinostat (Farydak).

In some embodiments, there are provided compounds of formula I:

I

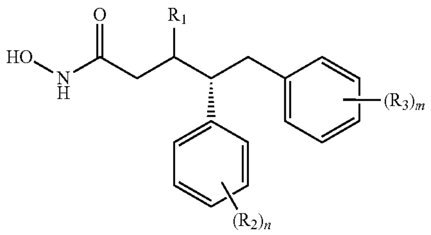

wherein $R_1$ is an alkoxy;

m is an integer from 0 to 5;

n is an integer from 0 to 5;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen;

each $R_3$ is independently selected from the group consisting of hydrogen, halogen, alkyl, alkenyl, carboxy, hydroxymethyl, amido; and wherein at least one of $R_2$ and $R_3$ is not hydrogen.

In some embodiments, $R_1$ is an alkoxy in the R-diastereomeric configuration.

In some embodiments, $R_1$ is an alkoxy in the S-diastereomeric configuration.

In some embodiments, $R_1$ is ethoxy or methoxy.

In some embodiments, m=1 and $R_3$ is 4-chloro.

In some embodiments, m is an integer from 0 to 2.

In some embodiments, n is an integer from 0 to 4.

In some embodiments, each $R_2$ is a halogen independently selected from the group consisting of fluorine, bromine, and chlorine.

In some embodiments, $R_2$ is a 4-substituted halogen.

In some embodiments, the $R_2$ heterocyclyl or hetereocyclylmethyl group comprises a morpholine, a piperazine, an oxirane, or a piperidine.

In some embodiments, there are provided compounds of formula II:

II

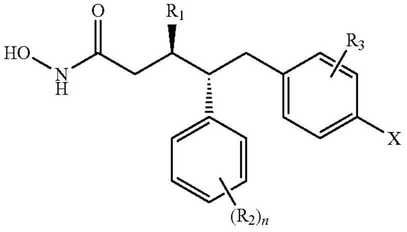

wherein $R_1$ is an alkoxy;

n is an integer from 0 to 5;

X is a halogen;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen; and $R_3$ is methyl or hydrogen.

In some embodiments, $R_1$ is methoxy or ethoxy.

In some embodiments, at least one $R_2$ is halogen.

In some embodiments, X is chlorine.

In some embodiments, x is fluorine.

In some embodiments, at least one $R_2$ is heterocyclyl or hetereocyclylmethyl.

In some embodiments, the heterocyclyl or hetereocyclylmethyl group comprises a morpholine, a piperazine, an oxirane, or a piperidine.

In some embodiments, there are provided compounds of formula III:

III

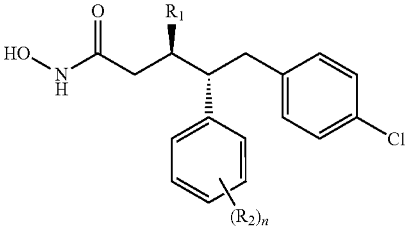

wherein $R_1$ is an alkoxy;

n is an integer from 0 to 5;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen.

In some embodiments, at least one $R_2$ is halogen.

In some embodiments, at least one $R_2$ is hydroxymethyl.

In some embodiments, at least on $R_2$ is heterocyclyl or hetereocyclylmethyl.

In some embodiments, there are provided compounds selected from any one of Examples 1 to 52 of Table 1.

In some embodiments, there are provided pharmaceutical composition comprising a compound according one or more of the previous embodiments along with a pharmaceutically acceptable carrier.

In some embodiments, there are provided methods of treating a subject exposed to a *botulinum* toxin comprising administering to the subject a pharmaceutical composition comprising a compound according to one or more of the previous embodiments.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —$C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [—CH═CH—]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, the alkyl group will comprise from 1 to 10 carbon atoms. In further embodiments, the alkyl group will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH2-). Unless otherwise specified, the term "alkyl" may include "alkylene" groups.

The terms "amido" is interchangeable with "carbamoyl," and as used herein, alone or in combination, refer to an amino group as described below attached to the parent molecular moiety through a carbonyl group, or vice versa. The term "C-amido" as used herein, alone or in combination, refers to a —C(O)—$NR_2$ group with R as defined herein. The term "N-amido" as used herein, alone or in combination, refers to a RC(O)NH— group, with R as defined herein. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "halo," or "halogen," as used herein, alone or in combination, refers to fluorine, chlorine, bromine, or iodine.

The term "heterocyclyl," as used herein, alone or in combination as in "heterocyclylmethyl", refers to a stable cyclic hydrocarbon group, fully saturated or containing from 1 to 3 degrees of unsaturation, consisting of from one to three heteroatoms chosen from O, N, and S, and wherein the nitrogen and sulfur atoms may optionally be oxidized and the nitrogen heteroatom may optionally be quaternized. The heterocycle groups may be optionally substituted unless specifically prohibited.

The term "hydroxyalkyl," as used herein, alone or in combination, refers to a hydroxy group attached to the parent molecular moiety through an alkyl group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N3, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof.

Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be phrased in terms of an IC50.

As used herein, reference to "treatment" or "treating" of a subject is intended to include prophylaxis. The term "subject" means all mammals including humans. In some embodiments, the patient is a human.

The term "compound," as used herein, includes salts, solvates and polymorphs of the compound, as well as the free base. In certain embodiments, the solvate is a hydrate. A solvate is a stable, solid or semi-solid form of a compound that comprises either a non-stoichiometric or a stoichimetric equivalent of solvent. If the solvent is water, the solvate is a hydrate. In certain embodiments, the hydrate has a stoichimetric equivalent of water chosen from about 0, about 0.5, and about 1 $H_2O$; that is, the hydrate is anhydrous, a hemihydrate, or a monohydrate. Non-stoichiometric hydrates and stoichiometric hydrates are both contemplated. As further discussed below, a polymorph is a distinct crystalline form of a compound. A compound may be, for example, a polymorph of a free base, a polymorph of a salt, a polymorph of a hydrate, or a polymorph of a hydrate of a salt of a compound, and so forth.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

These examples describe exemplary BoNT/A LC assays.

Assay A: In a 96 well, clear bottom black plate, the following was added to each well: 13 nM BoNT/A $LC_{1-429}$, 25 μM substrate in 30 mM HEPES pH 7.3, 0.05 mM zinc acetate, 0.05% Tween 20 for a total volume of 100 μL. Varying concentrations of inhibitor were added with a final DMSO concentration of 2.5%. The rate of enzymatic activity (RFU/sec) was monitored by a 30 minute kinetic read at ex 320 nm, em 420 nm.

Assay B: BoNT/A LC Assay Potent Range Conditions. In a 96 well, clear bottom black plate, the following was added to each well: 5 nM BoNT/A $LC_{1-429}$, 28 μM substrate in 30 mM HEPES pH 7.3, 0.05 mM zinc acetate, 0.05% Tween 20 for a total volume of 100 μL. Varying concentrations of inhibitor were added with a final DMSO concentration of 2.5%. The rate of enzymatic activity (RFU/sec) was monitored by a 60 minute kinetic read at ex 320 nm, em 420 nm.

Substrate: Abz-Thr-dArg-Ile-Asp-Glu-Ala-Asn-Gln-Arg-Ala-Thr-Lys-Nle-Lys(Dnp)-$NH_2$ (SEQ ID NO:1); $\lambda_{ex}$=320 nm, $\lambda_{em}$=420 nm HBI BoNT/A $LC_{1-429}$ construct (Hall A1):

BoNT/A $LC_{429}$ Enzymatic assay construct: MRHHHHHHGAQMPFVNKQFNYKDPVNGVDIAYIKIPNAGQMQPVKAFKIHNKIWVIPE RDTFTNPEEGDLNPPPEAKQVPVSYYDSTYLSTDNEKDNYLKGV TKLFERIYSTDLGR MLLTSIVRGIPFWGGSTIDTELKVIDTNCINVIQPDGSYRSEELNLVIIGPSADIIQFECKS FGHEVLNLTRNGYGSTQYIRFSPDFTFGFEESLEVDTNPLLGAGKFATDPAVTLAHELI HAGHRLYGIAINPNRVFKVNTNAYYEMSGLEVSFEELRTFGGHDAKFIDSLQENEFRLY YYNKFKDIASTLNKAKSIVGTTASLQYMKNVFKEKYLLSEDTSGKFSVDKLKFDKLYKM LTEIYTEDNFVKFFKVLNRKTYLNFDKAVFKINIVPKVNYTIYDGFNLRNTNLAANFNGQ NTEINNMNFTKLKNFTGLFEFYKLL (SEQ ID NO:2)

Table 1 below shows the results of application of these assays to small molecule hydroxamic acid compounds in accordance with embodiments herein.

TABLE 1

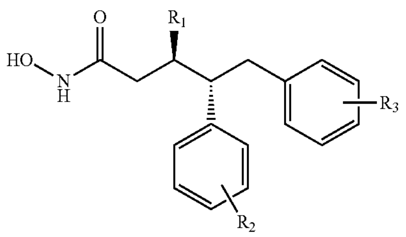

C5-Ph-$R^3$

| Example No. | $R^1$ | $R^2$ | $R^3$ | BoNT/A $K_i$ (nM) |
|---|---|---|---|---|
| 1-1 | OEt | 4-F | H | 38.5[a] |
| 1-2 | OEt | 4-F | 3-Br | 154[a] |
| 1-3 | OMe | 4-Br | 4-F | 9.36 |
| 1-4 | OEt | 4-F | 4-Br | 6.8[a] |
| 1-5 | OEt | 4-F | 4-CH═$CH_2$ | 33.5[a] |
| 1-6 | OEt | 4-F | 4-Et | 91.5[a] |
| 1-7 | OEt | 4-F | 4-C(O)—NHMe | 1220[a] |
| 1-8 | OEt | 4-F | 4-C(O)—$NMe_2$ | 4350[a] |
| 1-9 | OEt | 4-F | 4-$CH_2OH$ | 299 |
| 1-10 | OEt | 4-F | 4-$CO_2H$ | 23250[a] |
| 1-11 | OEt | 4-F | 3-(pyridin-4-yl) | 1060[a] |
| 1-12 | OEt | 4-F | 4-(pyridin-4-yl) | 178[a] |
| 1-13 | OEt | 4-F | 4-(pyridin-3-yl) | 147[a] |
| 1-14 | OEt | 4-F | 4-(5-methylpyridin-3-y) | 158[a] |

[a]data obtained under Assay A conditions; all other data obtained under Assay B conditions.

TABLE 2

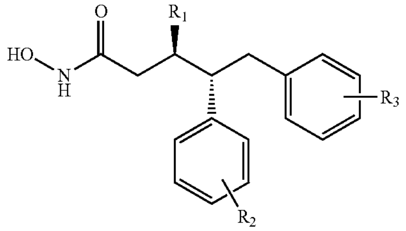

C5-Ph- polysubstituted

| Example No. | $R^1$ | $R^2$ | $R^3$ | BoNT/A $K_i$ (nM) |
|---|---|---|---|---|
| 2-1 | OMe | 4-Br | 2-Me-4-F | 235 |
| 2-2 | OMe | 4-Br | 3-Me-4-F | 3.4 |
| 2-3 | OMe (S) | 4-Br | 2-Me-4-F | 4855 |
| 2-4 | OMe (S) | 4-Br | 3-Me-4-F | 145 |

[a]data obtained under Assay A conditions; all other data obtained under Assay B conditions.

TABLE 3

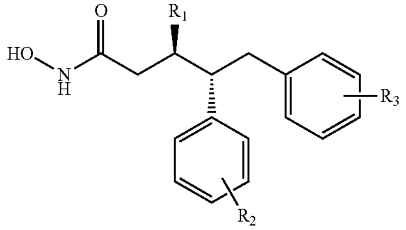

C4-Ph-$R^2$

| Example No. | $R^1$ | $R^2$ | $R^3$ | BoNT/A $K_i$ (nM) |
|---|---|---|---|---|
| 3-1 | OEt | H | 4-Cl | 15.5 |
| 3-2 | H | H | 4-Cl | 2700 |
| 3-3 | H | 4-Br | 4-Cl | 915 |
| 3-4 | OMe | 4-Cl | 4-Cl | 4.8 |
| 3-5 | OMe | 4-F | 4-Cl | 5.2 |
| 3-6 | OEt | 4-Br | 4-Cl | 2.0 ± 0.42 |
| 3-7 | OEt (S) | 4-Br | 4-Cl | 73 |
| 3-8 | OMe | 4-Br | 4-Cl | 1.75 |
| 3-9 | OEt | 4-CH═$CH_2$ | 4-Cl | 3.2 |
| 3-10 | OEt | 4-$CH_2OH$ | 4-Cl | 2.7 |
| 3-11 | OMe | 4-$CH_2OH$ | 4-Cl | 9.7 |
| 3-12 | OEt | 4-(-2-methyloxiran-2-yl) | 4-Cl | 9.6 |
| 3-13 | OMe | 4-($CH_2O(CH_2)_3CH_3$) | 4-Cl | 24.9 |
| 3-14 | OEt | 4-($CH_2OCH_2OCH_3$) | 4-Cl | 21.2 |
| 3-15 | OEt | 4-($CH_2OCH_2O$—($CH_2)_2OCH_3$) | 4-Cl | 30 |
| 3-16 | OEt | 4-($CH_2$-morpholin-1yl) | 4-Cl | 10.1 ± 2.4 |
| 3-17 | OEt | 4-($CH_2$-N-Boc-piperazin-1-yl) | 4-Cl | 8.5 |
| 3-18 | OEt | 4-($CH_2$-piperazin-1-yl) | 4-Cl | 13.5 ± 2.8 |
| 3-19 | OEt | 4-($CH_2$-piperidin-1-yl) | 4-Cl | 19.5 |
| 3-20 | OMe | 4-($CH_2$-piperidin-1-yl) | 4-Cl | 37 |
| 3-21 | OEt | 4-(N(Me)$CH_2CH_2OH$) | 4-Cl | 8.5 |
| 3-22 | OEt | 4-(piperazin-1-yl) | 4-Cl | 13.5 |
| 3-23 | OEt | 4-(morpholin-1-yl) | 4-Cl | 10.0 |
| 3-24 | OEt | 4-(N-Boc-2-pyrrol-2-yl) | 4-Cl | 8.8 |
| 3-25 | OEt | 4-(1H-pyrrol-2-yl) | 4-Cl | 8.0 |
| 3-26 | OEt | 4-(4-(pyrimidin-5-yl) | 4-Cl | 3.7 |
| 3-27 | OEt | 4-(2-(dimethylamino)pyrimidin-5-yl) | 4-Cl | 5.3 |
| 3-28 | OEt | 4-(1,3,5-trimethyl-1H-pyrazol-4-yl) | 4-Cl | 3.7 |
| 3-29 | OEt | 4-(1H-imidazol-1-yl) | 4-Cl | 3.6 |
| 3-30 | OEt | 4-(pyridine-4-yl) | 4-Cl | 4.5 |

[a]data obtained under Assay A conditions; all other data obtained under Assay B conditions.

TABLE 4

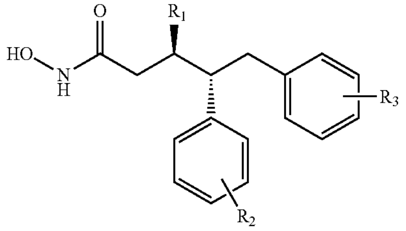

C4-Ph-amides

| Example No. | $R^1$ | $R^2$ | $R^3$ | BoNT/A $K_i$ (nM) |
|---|---|---|---|---|
| 4-1 | OEt | 4-C(O)NHOH | 4-Cl | 10.5 |
| 4-2 | OEt | 4-C(O)—N$(nPr)_2$ | 4-Cl | 3.9 |
| 4-3 | OEt | 4-C(O)-piperidin-1-yl | 4-Cl | 4.3 ± 2.0 |
| 4-4 | OEt | 4-C(O)N(Me)$CH_2CH_2OH$ | 4-Cl | 9.8 ± 3.7 |
| 4-5 | OEt | 4-C(O)-morpholin--1yl | 4-Cl | 5.8 ± 1.1 |
| 4-6 | OMe | 4-C(O)-morpholin-1-yl | 4-Cl | 11.4 |
| 4-7 | OMe | 4-C(O)-piperidin-1-yl | 4-Cl | 5.5 |
| 4-8 | OEt | 4-C(O)-N-Boc-piperazin-1-yl | 4-Cl | 22 |
| 4-9 | OEt | 4-C(O)—N—H-piperazin-1-yl | 4-Cl | 9.2 ± 6.1 |
| 4-10 | OEt | 4-C(O)N(Me)$(CH_2CH_2OH)_2$ | 4-Cl | 16.7 |

[a]data obtained under Assay A conditions; all other data obtained under Assay B conditions.

TABLE 5

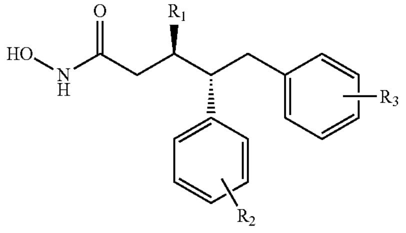

C4-Ph-polysubstituted

| Example No. | $R^1$ | $R^2$ | $R^3$ | BoNT/A $K_i$ (nM) |
|---|---|---|---|---|
| 5-1 | OMe | 3-Br-4-Cl | 4-Cl | 5.2 |
| 5-2 | OMe | 3-($CH_2$-piperidin-1-yl)-4-Cl | 4-Cl | 3.7 |
| 5-3 | OMe | 3-(C(O)-piperidin-1-yl)-4-Cl | 4-Cl | 13.1 |
| 5-4 | OMe | 2,4-diF | 4-Cl | 3.95 |
| 5-5 | OMe | 3,4,5-triF | 4-Cl | 5.36 |
| 5-6 | OMe | 2,3,4,5-tetraF | 4-Cl | 4.95 |

[a]data obtained under Assay A conditions; all other data obtained under Assay B conditions.

TABLE 6

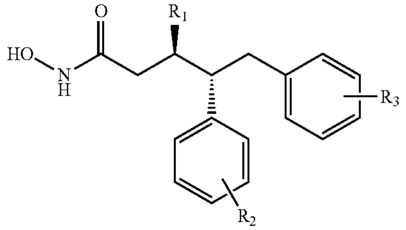

| Example No. | $R^1$ | $R^2$ | $R^3$ | BoNT/A $K_i$ (nM) |
|---|---|---|---|---|
| 6-1 | OEt | 4-Cl | 4-Cl | 4.9 |
| 6-2 (K salt) | OMe | 4-F | 4-Cl | 13.0 |
| 6-3 (K Salt) | OEt | 4-F | 4-Cl | 8.90 |
| C5-Ph-poly-substituted | | | | |
| 6-4 | OMe | 4-F | 2-Me-4-Cl | 1.48 |
| 6-5 (K salt) | OMe | 4-F | 2-Me-4-Cl | 3.88 |
| 6-6 | OEt | 4-Br | 2,4-diCl | 4.90 |
| C4-Ph-amides | | | | |
| 6-7 | OMe | 4-C(O)N(diMe) | 4-Cl | 26.2 |
| C4-Ph-poly-substituted | | | | |
| 6-8 | OMe | 2-F-4-($CH_2$-morpholin-1-yl) | 2-Me-4-Cl | 45.8 |
| 6-9 | OEt | 3-morpholino-4-Cl | 4-Cl | 5.8 |
| 6-10 | OEt | 2,4-diF | 2-Me-4-Cl | 10.0 |
| 6-11 | OEt | 2,4-diF | 4-Cl | 10.3 |
| 6-12 | OMe | 2,4-diF | 2,4-diF | 29.5 |
| 6-13 | OBn | 2,4-diF | 4-Cl | 114 |
| 6-14 | OEtOMe | 2,4-diF | 4-Cl | 55.1 |
| 6-15 | OBu | 2,4-diF | 4-Cl | 48.5 |
| 6-16 | OPr | 2,4-diF | 4-Cl | 38.5 |
| 6-17 | O($CH_2$-cyc-Pr) | 2,4-diF | 4-Cl | 52.4 |
| 6-18 | $O(CH_2)_2OH$ | 2,4-diF | 4-Cl | 8.75 |
| 6-19 | $O(CH_2)_3OH$ | 2,4-diF | 4-Cl | 1.45 |
| 6-20 (K salt) | OMe | 2,4-diF | 4-Cl | 8.30 |
| 6-21 (K salt) | OEt | 2,4-diF | 4-Cl | 12.0 |
| 6-22 (K salt) | OMe | 2,4-diF | 2-Me-4-Cl | 6.70 |
| 6-23 | OMe | 2-F-4-Br | 2-Me-4-Cl | 1.94 |
| 6-24 | OEt | 3-Br-4-Cl | 4-Cl | 8.1 |
| 6-25 | $O(CH_2)_3NH$-butyloxy-carbonyl | 2,4-diF | 4-Cl | >150,000 |
| 6-26 | $O(CH_2)_3NH_2$ | 2,4-diF | 4-Cl | 55,000 |
| 6-27 | $O(CH_2)_2CO_2H$ | 2,4-diF | 4-Cl | 361 |

all data obtained under Assay B conditions.

Table 7 below summarizes the abbreviations used in conjunction with Synthetic Schemes I-V below.

TABLE 7

| | |
|---|---|
| DMF | dimethylformamide |
| DCM | dichloromethane |
| DCE | 1,2-dichloroethane |
| DMSO | dimethyl sulfoxide |
| DMPAO | 2-(2,6-dimethylphenylamino)-2-oxoacetic acid |
| pyBOP | benzotriazol-1-yl-oxy-tris-pyrrolidino-phosphonium hexafluorophosphate |

TABLE 7-continued

| | |
|---|---|
| EtOAc | ethyl acetate |
| THF | tetrahydrofuran |
| DIEA | N,N-diisopropylethylamine |
| Jones oxidation reagent | $H_2CrO_4/H_2SO_4/H_2O$ |
| DMP | Dess-Martin periodinane |
| n-BuLi | n-Butyllithium |
| MeOH | methanol |
| LAH | lithium aluminum hydride |
| TMS | trimethylsilyl |
| Xc | chiral auxiliary |
| Ipc | isopinocampheyl |
| HMDS | hexamethyldisilazide |
| IR | infared spectroscopy |
| MS(EI) | mass spectrometry(electron impact) |
| Oet | ethoxy ($—OCH_2CH_3$) |
| Ome | methoxy ($—OCH_3$) |
| Oac | acetate ($OC(O)CH_3$) |
| $Ph_3P$ or $PPh_3$ | triphenylphosphine |
| EtOH | ethanol |
| $Et_2O$ | diethyl ether |
| MS(API-ES) | mass spectrometry(atmospheric pressure ionization-electrospray) |

Synthesis of exemplary compounds-Scheme I

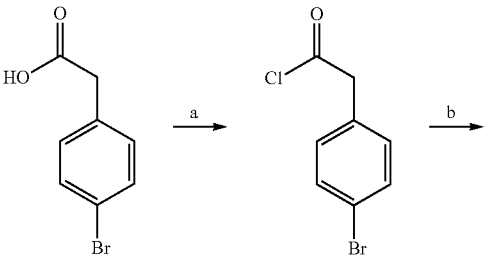

Intermediate A1

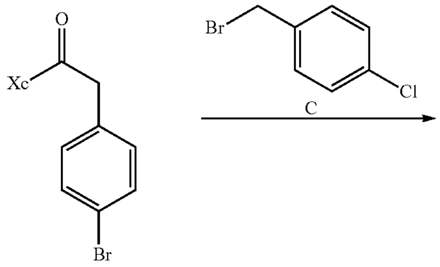

Intermediate B1

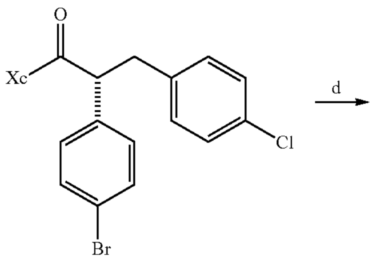

Intermediate C1

-continued

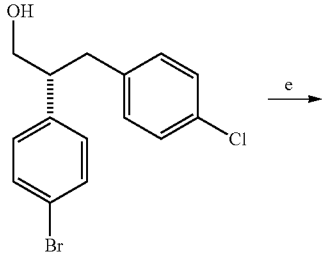

Intermediate D1

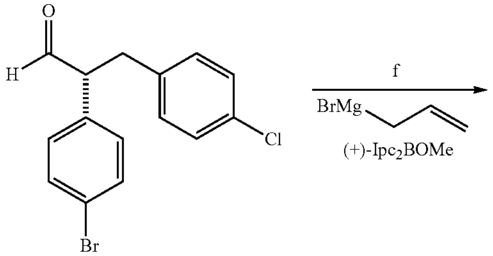

Intermediate E1

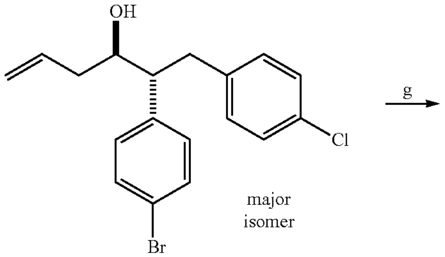

Intermediate F1

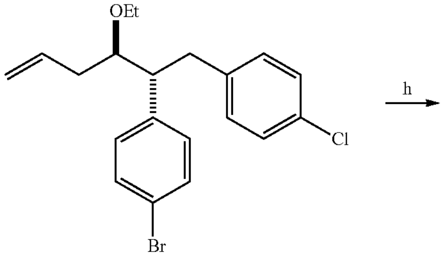

Intermediate G1

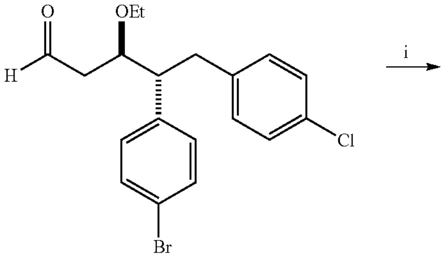

Intermediate H1

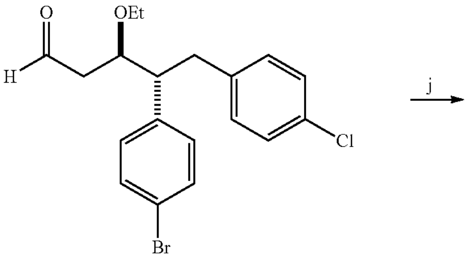

Intermediate I1

-continued

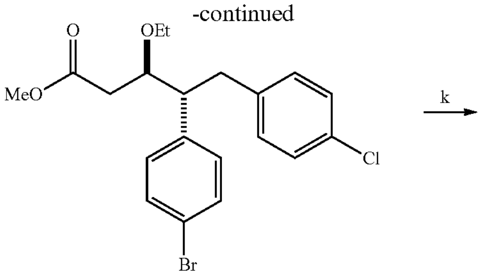

Intermediate J1

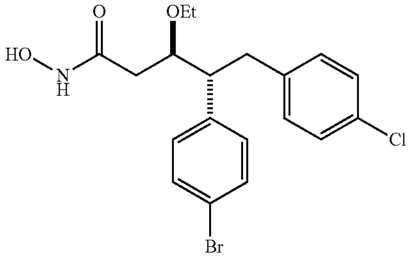

Compound 3-6

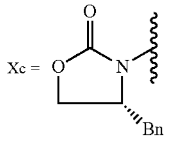

Reagents and conditions: a) oxalyl chloride, DMF, DCM, 25° C., three hours; b) (R)-4-Benzyl-2-oxazolidinone, nBuLi, THF, −78° C. to 0° C., three hours; c) LiHMDS, THF, −78° C. to −30° C., 16 hours; d) LAH, THF, 0° C. to 25° C., three hours; e) DMP, DCM, 25° C., three hours; f) $Et_2O$, −78 to 25° C., 16 hours, or allylmagnesium bromide, THF, −78° C.; g) EtI, NaH, DMF, 0 to 25° C., three hours; h) $O_3$, $Ph_3P$, DCM, −78 to 25° C., three hours; i) Jones oxidation reagent, acetone, 25° C., 20 min; j) $TMSCHN_2$, DCM, MeOH, 25° C., 30 min; k) $NH_2OH$, KCN, MeOH, THF, $H_2O$, 25° C., 24 hours.

2-(4-bromophenyl)acetyl chloride (Intermediate A1): To a solution of 2-(4-bromophenyl)acetic acid (10.0 g, 46 mmol) in DCM (150 mL) was slowly added oxalyl chloride (28 mL, 2M in DCM, 56 mmol) followed by DMF (20 μL). The reaction mixture was then stirred at ambient temperature for three hours and concentrated in vacuo to afford 2-(4-bromophenyl)acetyl chloride as a light yellow liquid. The crude product was used for the next step without further purification. IR (film) 1790, 1489, 1407, 1318, 1180, 1072, 1013, 959 $cm^{-1}$.

(R)-4-benzyl-3-(2-(4-bromophenyl)acetyl)oxazolidin-2-one (Intermediate B1) To a solution of (R)-4-benzyloxazolidin-2-one (9.9 g, 56 mmol) in THF (300 mL) at −78° C. was added n-BuLi (35 mL, 1.6 M in hexanes, 56 mmol). The resulting solution was stirred at −78° C. for 30 min. A solution of 2-(4-bromophenyl)acetyl chloride (46 mmol) in THF (50 mL) was then added dropwise and the reaction mixture was stirred for one hour at −78° C., then slowly warmed to 0° C. A saturated solution of $NH_4Cl$ (200 mL) was added and the organic layer was separated, The aqueous layer was extracted with EtOAc (3×150 mL). The combined organic extracts were washed with brine (2×100 mL), dried over $Na_2SO_4$, and evaporated under reduced pressure. The residue was purified by flash chromatography on silica gel eluting with 0-30% EtOAc/hexanes to yield 13.4 g (79.5%) of the title compound. MS(EI) m/z 373 ($M^+$), 196 ($M^+$-176)

base peak; IR (dry film) 1779, 1695, 1489, 1393, 1361, 1252, 1198, 1107, 1012 $cm^{-1}$.

(R)-4-benzyl-3-((R)-2-(4-bromophenyl)-3-(4-chlorophenyl)propanoyl)oxazolidin-2-one (Intermediate C1): To a solution of (R)-4-benzyl-3-(2-(4-bromophenyl)acetyl) oxazolidin-2-one (13.0 g, 35 mmol) in THF (180 mL) at −78° C. was added LiHMDS (42 mL, 1.0 M in THF, 42 mmol) dropwise and the resultant solution was stirred at −78° C. for 30 minutes. 1-(bromomethyl)-4-chlorobenzene (10.7 g, 52.5 mmol) was then added at −78° C. dropwise and kept at −20° C. for 16 hours before being quenched with a saturated solution of $NH_4Cl$ (200 mL). The crude reaction was extracted with EtOAc (3×100 mL), and the combined organic extracts were dried over $Na_2SO_4$ and concentrated in vacuo. Purification by flash chromatography on silica gel eluting with 5-30% EtOAc/hexanes and recrystallization ($Et_2O$) afforded 12.3 g (70.4%) of the desired product as a white solid, dr>96:4, MS(EI) m/z 497 ($M^+$), 117 ($M^+$-380) base peak; IR (dry film) 1778, 1694, 1488, 1389, 1367, 1211, 1097, 1011, 817 $cm^{-1}$.

(R)-2-(4-bromophenyl)-3-(4-chlorophenyl)propan-1-ol (Intermediate D1): A solution of (R)-4-benzyl-3-((R)-2-(4-bromophenyl)-3-(4-chlorophenyl)propanoyl)oxazolidin-2-one (3.7 g, 7.4 mmol) in THF (35 mL) was added LAH (22.2 mL, 1.0 M in THF, 22.2 mmol) dropwise at −4° C. The solution was stirred for an additional three hours, and the temperature was slowly increased to room temperature during the period. Then, the reaction mixture was carefully quenched with 4% $H_2SO_4$, and pH was adjusted to 4 with more 4% $H_2SO_4$. The resulting mixture was extracted with EtOAc (3×60 mL), and the combined organic extracts were washed with 4% $H_2SO_4$ (30 mL) and brine (2×40 mL). After drying over $Na_2SO_4$, the extracts were concentrated in vacuo. Purification by flash chromatography on silica gel eluting with 5-50% EtOAc/hexanes afforded 1.9 g (80.4%) of the desired product as a colorless oil. MS(EI) m/z 324 ($M^+$), 120 ($M^+$-204) base peak; IR (film) 1359, 2929, 1489, 1407, 1092, 1073, 1009, 821 $cm^{-1}$.

(R)-2-(4-bromophenyl)-3-(4-chlorophenyl)propanal (Intermediate E1): To a solution of (R)-2-(4-bromophenyl)-3-(4-chlorophenyl)propan-1-ol (1.8 g, 5.8 mmol) in DCM (70 mL) at 25° C. was slowly added Dess-Martin periodinane (3.6 g, 8.6 mmol). The reaction was stirred at 25° C. for three hours, then quenched by addition of saturated $NaHCO_3$ (50 mL). The organic phase was separated and the aqueous phase was extracted with DCM (3×50 mL). The combined organic layers were washed with brine and dried over $Na_2SO_4$. The solvent was evaporated under reduced pressure and the residue was used for the next step without further purification. MS(EI) m/z 322 ($M^+$), 125 ($M^+$-195) base peak.

(2R,3R)-2-(4-bromophenyl)-1-(4-chlorophenyl)hex-5-en-3-ol (Intermediate F1) A solution of (+)-B-methoxydiisopinocampheylborane ((+)-$(Ipc)_2$BOMe) (1.9 g, 6.1 mmol) in $Et_2O$ (10 mL) was cooled to 0° C. and vigorously stirred. An allylmagnesium bromide solution (6.1 mL, 1.0 M in $Et_2O$, 6.1 mmol) was then added dropwise. After the addition was complete, the reaction mixture was vigorously stirred for one hour at room temperature. The resulting solution of (+)-$(Ipc)_2$B(allyl) was cooled to −78° C. under vigorous stirring, then a solution of (R)-2-(4-bromophenyl)-3-(4-chlorophenyl)propanal in $Et_2O$ (15 mL) was added dropwise. The resulting mixture was vigorously stirred at −78° C. for three hours, and allowed to warm to room temperature over three hours. The mixture was stirred for another 12 hours. The reaction mixture was cooled to 0° C. and a premixed solution of 3N NaOH (6 mL) and 30% $H_2O_2$ (2 mL) was carefully added over 10 minutes. The resulting biphasic mixture was refluxed for two hours with vigorous stirring. The reaction mixture was cooled to room temperature, the organic phase was separated, and the aqueous phase was extracted with $Et_2O$ (2×30 mL). The combined organic layers were washed with brine (2×30 mL), dried over $Na_2SO_4$, and filtered. The filtrate was concentrated under reduced pressure to give a light yellow residue. This mixture was purified by flash chromatography eluting with 0-30% EtOAc/hexanes on silica gel to provide the allyl alcohol as a colorless oil. MS(EI) m/z 364 ($M^+$), 346 ($M^+$-$H_2O$), 125 ($M^+$-239) base peak; IR (film) 3412, 2926, 1639, 1489, 1221, 1092, 1009, 920, 821 $cm^{-1}$.

Alternatively, to a solution of (R)-2-(4-bromophenyl)-3-(4-chlorophenyl)propanal (Intermediate E1) (3.8 mmol) in THF (30 mL) cooled to −78° C., was added allylmagnesium bromide solution (1.0 M in $Et_2O$, 6.0 mL, 6.0 mmol). After stirring for two hours, the reaction was quenched with addition of saturated $NH_4Cl$. The resultant mixture was extracted with EtOAc (3×50 mL). The combined organic layers were washed with brine (2×30 mL), and dried over $Na_2SO_4$. Purification of the crude material via flash chromatography on silica gel (0-20% EtOAc/hexanes) afforded 627 m (45.3%) of the desired product, dr>68:32, MS(EI) m/z 364 ($M^+$), 346 ($M^+$-H2O), 125 ($M^+$-239) base peak; IR (film) 3412, 2926, 1639, 1489, 1221, 1092, 1009, 920, 821 $cm^{-1}$.

1-bromo-4-((2R,3R)-1-(4-chlorophenyl)-3-ethoxyhex-5-en-2-yl)benzene (Intermediate G1): To a solution of (2R, 3R)-2-(4-bromophenyl)-1-(4-chlorophenyl)hex-5-en-3-ol (2.7 mmol) in DMF (15 mL), cooled to 0° C., was added sodium hydride (648 mg, 16.2 mmol). After stirring for five minutes, ethyl iodide (2.1 g, 13.7 mmol) was added and the reaction was allowed to warm to room temperature. After three hours, the reaction was quenched with very slow addition of saturated NH4Cl. The resulting mixture was extracted with EtOAc (3×50 mL). The combined organic layers were washed with brine (2×30 mL) and dried over $Na_2SO_4$. Purification of the crude material via flash chromatography on silica gel (0-15% EtOAc/hexanes) afforded 956 mg (87.8%) of the ether as a light yellow oil. MS(EI) m/z 392 ($M^+$), 99 ($M^+$-292) base peak.

(3R,4R)-4-(4-bromophenyl)-5-(4-chlorophenyl)-3-ethoxypentanal (Intermediate H1): A solution of 1-bromo-4-((2R,3R)-1-(4-chlorophenyl)-3-ethoxyhex-5-en-2-yl)benzene (1.0 g, 2.6 mmol) in DCM (30 mL) was cooled to −78° C. Then $O_3$ was bubbled through the reaction until the solution turned blue. The reaction mixture was then sparged with argon. Triphenylphosphine (2.6 g, 10.2 mmol), was added. The solution was allowed to slowly warm to room temperature over one hour. After two hours of additional stirring at room temperature, the solution was concentrated by in vacuo. The residue was purified by flash chromatography on silica gel eluting with 0-20% EtOAc/hexanes to afford 847 mg (82.6%) of the desired product as a light yellow oil. MS(EI) m/z 394 ($M^+$), 101 ($M^+$-292) base peak; IR (film) 2974, 2727, 1722, 1489, 1406, 1094, 1074, 1010, 823 $cm^{-1}$.

(3R,4R)-4-(4-bromophenyl)-5-(4-chlorophenyl)-3-ethoxypentanoic acid (Intermediate 11): To a solution of (3R,4R)-4-(4-bromophenyl)-5-(4-chlorophenyl)-3-ethoxypentanal (847 mg, 2.1 mmol) in acetone (8 mL) was added prepared Jones oxidation reagent. The addition was continued until the characteristic orange color of the reagent persisted for approximately 20 minutes. The reaction mixture was diluted with water (20 mL) and DCM (20 mL) and the layers were separated. The aqueous layer was extracted with additional DCM (20 mL). The combined organic layers were washed with brine (2×20 mL) and dried over $Na_2SO_4$. The solution was concentrated under reduced pressure. The residue was used to prepare methyl (3R,4R)-4-(4-bromophenyl)-5-(4-chlorophenyl)-3-ethoxypentanoate without further purification.

(3R,4R)-4-(4-bromophenyl)-5-(4-chlorophenyl)-3-ethoxypentanoate (Intermediate J1): A solution of (3R,4R)-4-(4-bromophenyl)-5-(4-chlorophenyl)-3-ethoxypentanoic acid (2.1 mmol) in MeOH (1 mL) and DCM (9 mL) at room temperature was slowly treated with 2M trimethylsilyldiazomethane in hexanes until the solution became light yellow. The mixture was concentrated to provide the crude product. The residue was purified by flash chromatography on silica gel eluting with 0-15% EtOAc/hexanes to yield 678 mg (76.1%) of the title compound. MS(EI) m/z=424 ($M^+$), 131 ($M^+$-292) base peak; IR (dry film) 2974, 1738, 1489, 1436, 1163, 1093, 1074, 1010, 822 $cm^{-1}$.

(3R,4R)-4-(4-bromophenyl)-5-(4-chlorophenyl)-3-ethoxy-N-hydroxypentanamide (Compound 3-6): To a solution of (3R,4R)-4-(4-bromophenyl)-5-(4-chlorophenyl)-3-ethoxypentanoate (120 mg, 0.28 mmol) in 10 mL of THF, MeOH, and 50 wt % $NH_2OH$ in $H_2O$ (2:2:1) was added KCN (20 mg). The resulting mixture stirred for 2 days at room temperature. Evaporation of solvent left the crude product mixture from which the product was isolated by flash chromatography on silica gel eluting with 0-40% EtOH/DCM to give 91 mg (75.8%) of the title compound as a white solid, 75.8%. MS (API-ES) m/z 425 ($M+H^+$) IR (dry film) 3227, 2975, 2926, 2892, 1652, 1492, 1092, 1074, 1010, 822 $cm^{-1}$.

Synthesis of exemplary compounds-Scheme II

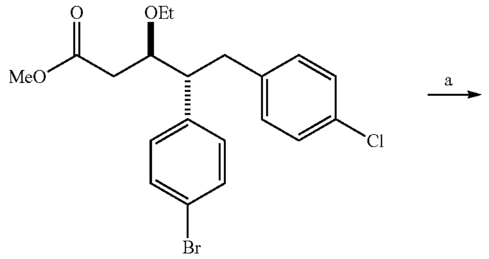

Intermediate J1

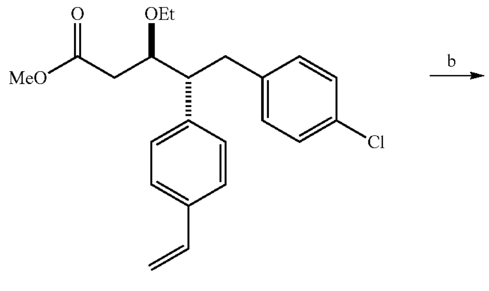

Intermediate A2

-continued

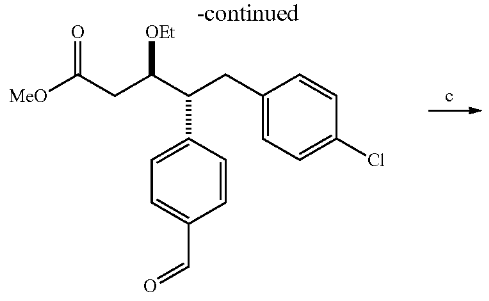

Intermediate B2

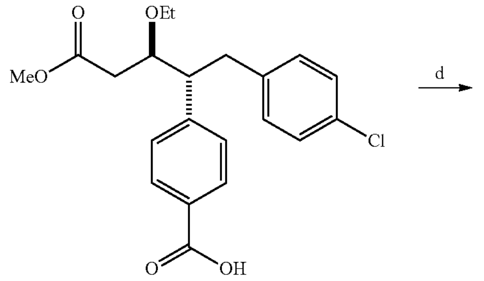

Intermediate C2

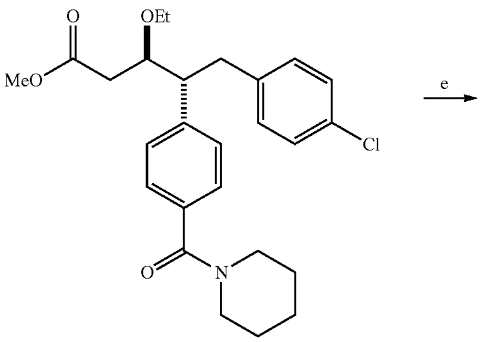

Intermediate D2

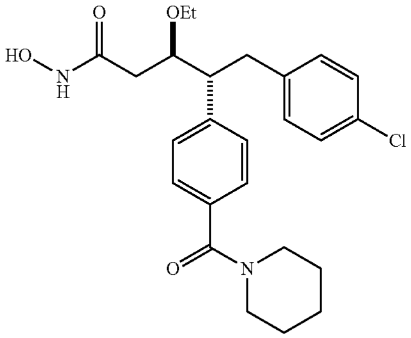

Compound 4-3

Reagents and conditions: a) Tributyl(vinyl)tin, $Pd(PPh_3)_4$, toluene, 80° C., 16 hours; b) $O_3$, $Ph_3P$, DCM, −78° C. to 25° C., 3 hours; c) Jones oxidation reagent, acetone, 25° C., 3 hours; d) piperidine, pyBOP, DMF, 25° C., 12 hours; e) $NH_2OH$, KCN, MeOH, THF, $H_2O$, 25° C., 24 hours.

Methyl (3R,4R)-5-(4-chlorophenyl)-3-ethoxy-4-(4-vinylphenyl)pentanoate (Intermediate A2): To a mixture of (3R,4R)-4-(4-bromophenyl)-5-(4-chlorophenyl)-3-ethoxypentanoate (424 mg, 1.0 mmol) and $Pd(PPh_3)_4$ (23 mg, 0.02 mmol) in toluene (10 mL) was added tributyl(vinyl)tin compound (602 mg, 1.9 mmol) at ambient temperature. The mixture was stirred at 80° C. for 16 hours. After cooling, the reaction mixture was evaporated under reduced pressure. The crude product was purified by flash chromatography on silica gel eluting with 0-20% EtOAc/hexanes to give 267 mg (72%) of the title compound as a colorless oil. MS(EI) m/z 326 ($M^+$-OEt), 89 ($M^+$-283) base peak.

Methyl (3R,4R)-5-(4-chlorophenyl)-3-ethoxy-4-(4-formylphenyl)pentanoate (Intermediate B2): A solution of methyl (3R,4R)-5-(4-chlorophenyl)-3-ethoxy-4-(4-vinylphenyl) pentanoate (420 mg, 1.1 mmol) in DCM (20 mL) was cooled to −78° C. Then $O_3$ was bubbled through the reaction until the solution turned blue. The reaction mixture was then sparged with argon. Triphenylphosphine (1.2 g, 4.5 mmol), was added. The solution was allowed to slowly warm to room temperature over one hour. After two hours of additional stirring at room temperature, the solution was concentrated by under reduced pressure. The residue was purified by flash chromatography on silica gel eluting with 0-20% EtOAc/hexanes to afford 387 mg (94.1%) of the desired product as a light yellow oil. MS(EI) m/z 374 ($M^+$), 89 ($M^+$-285) base peak; IR (film) 2952, 2736, 1725, 1696, 1606, 1491, 1437, 1212, 1170, 1093, 1015, 842 $cm^{-1}$.

4-((2R,3R)-1-(4-chlorophenyl)-3-ethoxy-5-methoxy-5-oxopentan-2-yl)benzoic acid (Intermediate C2): To a solution of methyl (3R,4R)-5-(4-chlorophenyl)-3-ethoxy-4-(4-formylphenyl)pentanoate (387 mg, 1.0 mmol) in acetone (4 mL) was added prepared Jones oxidation reagent. The mixture was heated to reflux and the addition of Jones oxidation reagent was continued until the characteristic orange color of the reagent persisted for about 20 minutes. Analysis of the reaction by TLC indicated the reaction was complete The reaction mixture was diluted with water (20 mL) and DCM (20 mL) and the layers were separated. The aqueous layer was extracted with DCM (2x20 mL). The combined organic layers were washed with brine (2x20 mL) and dried over $Na_2SO_4$. The solution was concentrated under reduced pressure. The residue was used without further purification. IR (dry film) 2952, 1738, 1695, 1558, 1436, 1287, 1180, 1099 $cm^{-1}$.

Methyl (3R,4R)-5-(4-chlorophenyl)-3-ethoxy-4-(4-(piperidine-1-carbonyl)phenyl)pentanoate (Intermediate D2): A solution of 4-((2R,3R)-1-(4-chlorophenyl)-3-ethoxy-5-methoxy-5-oxopentan-2-yl)benzoic acid (140 mg, 0.36 mmol), piperidine (107 mg, 1.3 mmol), benzotriazol-1-yl-oxy-tris-pyrrolidino-phosphonium hexafluorophosphate (PyBop; 303 mg, 0.72 mmol), and DIEA (438 □L, 2.5 mmol) in DMF (4 ml) was stirred at room temperature for 12 hours. The reaction was quenched with addition of saturated $NH_4Cl$. The resulting mixture was extracted with EtOAc (3x30 mL). The combined organic layers were washed with brine (2x15 mL), and dried over $Na_2SO_4$. Purification of the crude material via flash chromatography on silica gel (0-10% MeOH/DCM) afforded 118 mg (71.7%) of the amide as a light yellow oil. MS(EI) m/z 457 ($M^+$), 71 ($M^+$-386) base peak; IR (film) 2936, 2856, 1738, 1678, 1630, 1630, 1491, 1435, 1275, 1092, 1014, 844 $cm^{-1}$.

(3R,4R)-5-(4-chlorophenyl)-3-ethoxy-N-hydroxy-4-(4-(piperidine-1-carbonyl)phenyl)pentanamide (Compound 4-3): To a solution of methyl (3R,4R)-5-(4-chlorophenyl)-3-ethoxy-4-(4-(piperidine-1-carbonyl)phenyl)pentanoate (118 mg, 0.26 mmol) in 10 mL of THF, MeOH, and 50 wt % $NH_2OH$ in $H_2O$ (2:2:1) was added KCN (20 mg). The resulting mixture stirred for 2 days at room temperature. Evaporation of solvent left the crude product mixture from which the product was isolated by flash chromatography on silica gel eluting with 0-40% EtOH/DCM to give 91 mg (76.4%) of the title compound as a white solid. MS (API-ES) m/z 459 ($M+H^+$) IR (dry film): 3307, 3207, 2935, 2858, 1668, 1599, 1574, 1492, 1471, 1446, 1276, 1091 $cm^{-1}$.

Synthesis of exemplary compounds-Scheme III

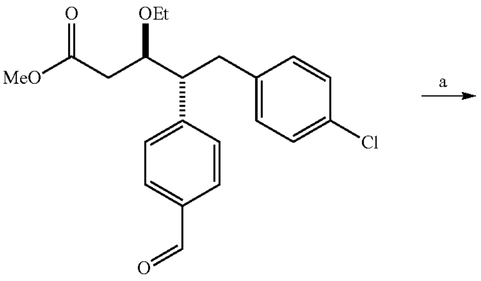

Intermediate B2

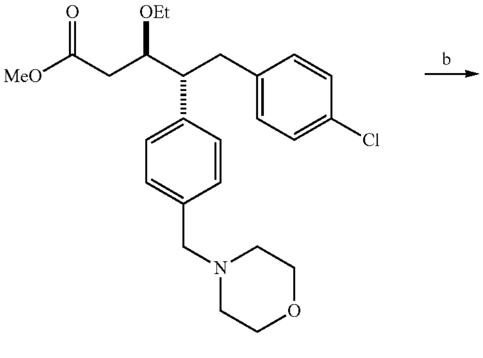

Intermediate A3

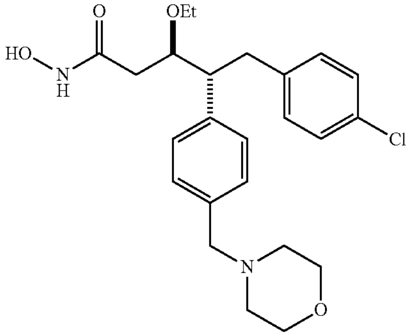

Compound 3-16

Reagents and conditions: a) morpholine, $NaBH(OAc)_3$, DCE, 25° C., 16 h; b) $NH_2OH$, KCN, MeOH, THF, $H_2O$, 25° C., 24 hours.

Methyl (3R,4R)-5-(4-chlorophenyl)-3-ethoxy-4-(4-(morpholinomethyl)phenyl)pentanoate (Intermediate A3): To a solution of methyl (3R,4R)-5-(4-chlorophenyl)-3-ethoxy-4-(4-formylphenyl) pentanoate (400 mg, 1.1 mmol) and morpholine (125 mg, 1.4 mmol) in DCE (6 mL), was added sodium triacetoxhydroborate (354 mg, 1.7 mmol) and acetic acid (86.4 mg, 1.4 mmol). The reaction mixture was stirred at room temperature for 16 h. The reaction solution was diluted with EtOAc and aqueous 5% NaOH solution. The mixture was extracted with more EtOAc (3x30 mL). The combined organic layers were washed with brine (2x30 mL), dried over $Na_2SO_4$, filtered and concentrated under reduced pressure. Purification of the crude material via flash chromatography on silica gel (0-10% MeOH/DCM) gave the desired compound as a light yellow oil (506 mg, 94.7%). MS(EI) m/z 445 ($M^+$), 71 ($M^+$-374) base peak; IR (film): 2971, 2805, 1738, 1492, 1455, 1366, 1117, 1093, 1015, 867 $cm^{-1}$.

(3R,4R)-5-(4-chlorophenyl)-3-ethoxy-N-hydroxy-4-(4-(morpholinomethyl)phenyl) pentanamide (Compound 3-16): To the solution of methyl (3R,4R)-5-(4-chlorophenyl)-3-ethoxy-4-(4-(morpholinomethyl)phenyl) pentanoate (506 mg, 1.1 mmol) in 10 mL of THF, MeOH, and 50 wt % $NH_2OH$ in $H_2O$ (2:2:1) was added KCN (20 mg). The resulting mixture stirred for 2 days at room temperature. Evaporation of solvent left the crude product mixture from which the product was isolated by flash chromatography on silica gel eluting with 0-45% EtOH/DCM to give the title compound as a white solid (431 mg, 85.5%).

MS (API-ES) m/z 447 $(M+H^+)$ IR (dry film): 3388, 3183, 1953, 2925, 2854, 1661, 1505, 1455, 1219, 1093, 1014, 969, 867, 837 $cm^{-1}$.

Synthesis of exemplary compounds-Scheme IV

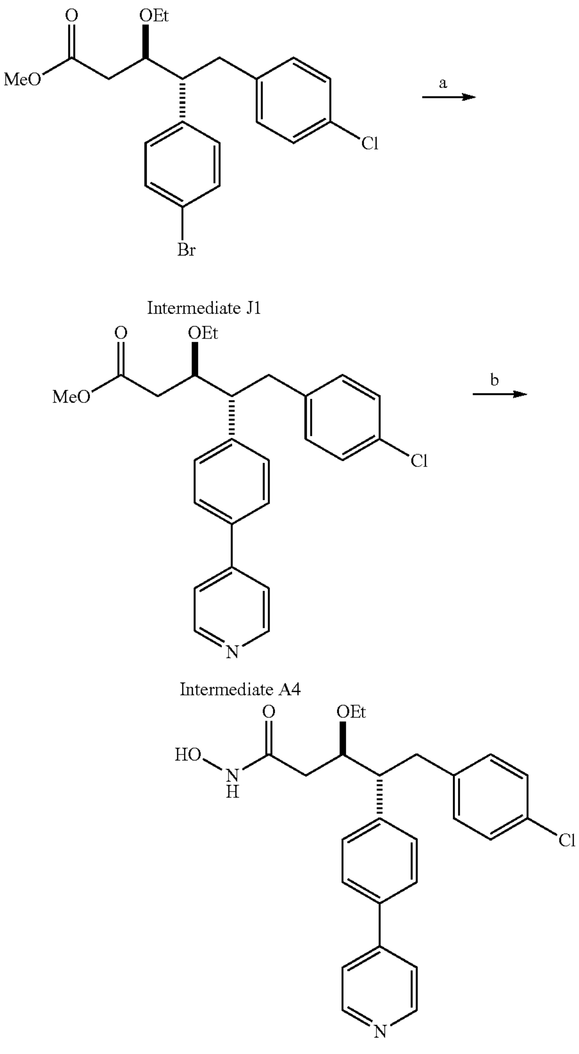

Intermediate J1

Intermediate A4

Compound 3-30

Reagents and conditions: a) 4-Pyridinylboronic acid, $Pd(Ph_3P)_4$, $K_2CO_3$, EtOH, THF, toluene, $H_2O$, 90° C., 12 hours, b) $NH_2OH$, KCN, MeOH, THF, $H_2O$, 25° C., 24 hours.

Methyl (3R,4R)-5-(4-chlorophenyl)-3-ethoxy-4-(4-(pyridin-4-yl)phenyl)pentanoate (Intermediate A4): (3R,4R)-4-(4-bromophenyl)-5-(4-chlorophenyl)-3-ethoxypentanoate (120 mg, 0.28 mmol), 4-pyridineboronic acid (40.2 mg, 0.33 mmol), $K_2CO_3$ (58 mg, 0.42 mmol), and $Pd(PPh_3)_4$ (6.5 mg, 0.0056 mmol) were dissolved with THF (1.5 mL), EtOH (1.5 mL), toluene (1.5 mL), and water (0.6 mL). The reaction mixture was stirred at 90° C. for 12 h. The reaction mixture was cooled to room temperature and concentrated under reduced pressure. The residue was purified by flash chromatography on silica gel eluting with 0-15% MeOH/DCM to give 97 mg (81.9%) of the title compound as a light yellow oil. IR (film) 3387, 3028, 2974, 2927, 1733, 1596, 1491, 1437, 1406, 1371, 1230, 1159, 1093, 1014, 813 $cm^{-1}$.

(3R,4R)-5-(4-chlorophenyl)-3-ethoxy-N-hydroxy-4-(4-(pyridin-4-yl)phenyl)pentanamide (Compound 3-30): To a solution of methyl methyl (3R,4R)-5-(4-chlorophenyl)-3-ethoxy-4-(4-(pyridin-4-yl)phenyl)pentanoate (97 mg, 0.23 mmol) in 5 mL of THF, MeOH, and 50 wt % $NH_2OH$ in $H_2O$ (2:2:1) was added KCN (10 mg). The resulting mixture was stirred for 2 days at room temperature. The reaction mixture was concentrated under reduced pressure and the crude product was purified by flash chromatography on silica gel eluting with 0-45% EtOH/DCM to give the title compound as a white solid (43 mg, 44.1%). MS (API-ES) m/z 425 $(M+H^+)$; IR (dry film): 3345, 3144, 3064, 2977, 2864, 1710, 1653, 1607, 1491, 1326, 1090, 993, 814 $cm^{-1}$.

Synthesis of exemplary compounds-Scheme V

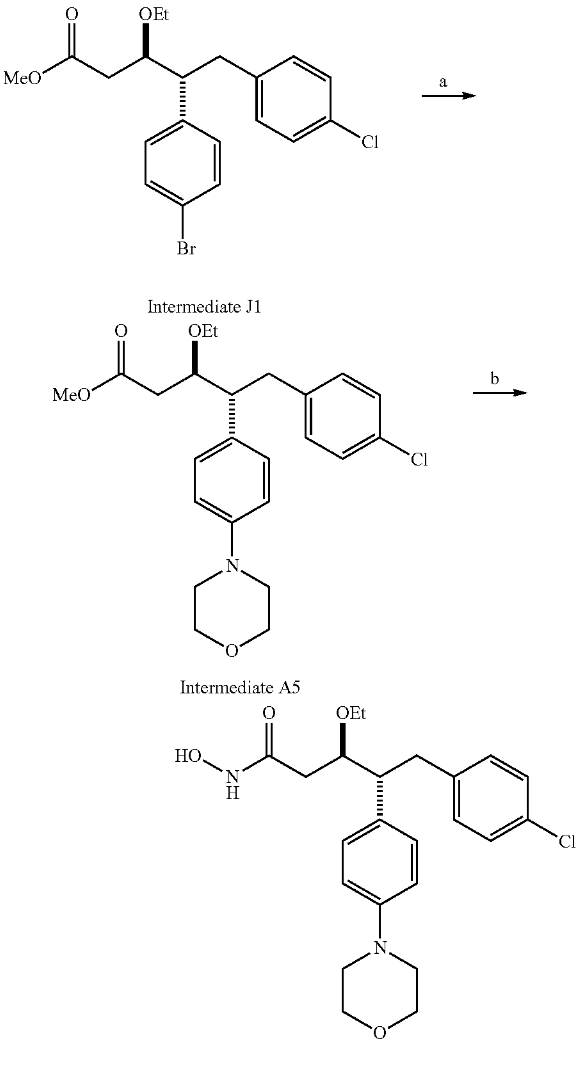

Intermediate J1

Intermediate A5

Compound 3-23

Reagents and conditions: a) morpholine, DMPAO, CuI, $K_3PO_4$, DMSO, 90° C., 24 hours; b) $NH_2OH$, KCN, MeOH, THF, $H_2O$, 25° C., 24 hours.

Methyl (3R,4R)-5-(4-chlorophenyl)-3-ethoxy-4-(4-morpholinophenyl) pentanoate (Intermediate A5): To (3R,4R)-4-(4-bromophenyl)-5-(4-chlorophenyl)-3-ethoxypentanoate (100 mg, 0.23 mmol) was added CuI (4.3 mg, 0.023 mmol), DMPAO (8.8 mg, 0.046 mmol), and $K_3PO_4$ (62.5 mg, 0.46 mmol) at ambient temperature. The tube was evacuated and backfilled with argon, and then morpholine (30.5 mg, 0.35 mmol) and DMSO (1 mL) was added. The reaction mixture was stirred at 90° C. for 24 h. After (3R,4R)-4-(4-bromophenyl)-5-(4-chlorophenyl)-3-ethoxypentanoate was consumed, water was added and the mixture was extracted with EtOAc (3×20 mL). The combined organic layers were dried over $Na_2SO_4$ and evaporated. The residue was purified by flash chromatography on silica gel to give the desired product as a light yellow oil (43 mg, 43.3%).

(3R,4R)-5-(4-chlorophenyl)-3-ethoxy-N-hydroxy-4-(4-morpholinophenyl)pentanamide (Compound 3-23): To a solution of methyl (3R,4R)-5-(4-chlorophenyl)-3-ethoxy-4-(4-morpholinophenyl)pentanoate (43 mg, 0.10 mmol) in 5 mL of THF, MeOH, and 50 wt % $NH_2OH$ in $H_2O$ (2:2:1) was added KCN (10 mg). The resulting mixture was stirred for 2 days at room temperature. Evaporation of solvent left the crude product mixture from which the product was isolated by flash chromatography on silica gel eluting with 0-45% EtOH/DCM to give the title compound as a white solid (4.8 mg, 11.1%). MS (API-ES) m/z 433 ($M+H^+$); IR (dry film): 2956, 2924, 2854, 1652, 1615, 1557, 1456, 1377, 1234, 1162, 1082 $cm^{-1}$.

Characterizing Data for Exemplary Compounds

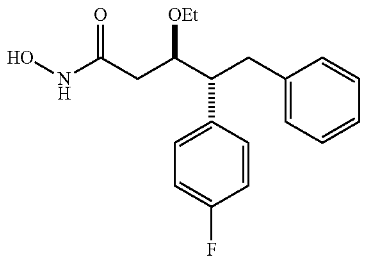 [SMILES: CCO[C@H](CC(=O)NO)[C@H](Cc1ccccc1)c1ccc(F)cc1]

(3R,4R)-3-ethoxy-4-(4-fluorophenyl)-N-hydroxy-5-phenylpentanamide (Compound 1-1)

MS (API-ES) m/z 332 ($M+H^+$); IR: 3176, 2974, 2871, 1652, 1622, 1511, 1454, 1222, 1159, 1083, 834 $cm^{-1}$.

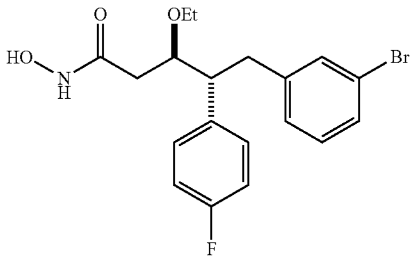 [SMILES: CCO[C@H](CC(=O)NO)[C@H](Cc1cccc(Br)c1)c1ccc(F)cc1]

(3R,4R)-5-(3-bromophenyl)-3-ethoxy-4-(4-fluorophenyl)-N-hydroxypentanamide (Compound 1-2): MS (API-ES) m/z 410 ($M+H^+$); IR: 3221, 2975, 2926, 2880, 1652, 1511, 1472, 1223, 1159, 1086, 834, 780 $cm^{-1}$.

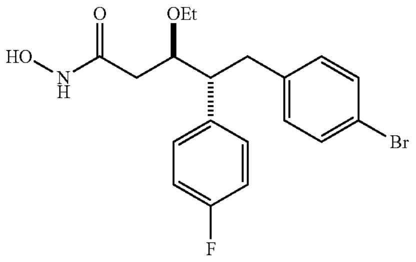 [SMILES: CCO[C@H](CC(=O)NO)[C@H](Cc1ccc(Br)cc1)c1ccc(F)cc1]

(3R,4R)-5-(4-bromophenyl)-3-ethoxy-4-(4-fluorophenyl)-N-hydroxypentanamide (Compound 1-4): MS (API-ES) m/z 410 ($M+H^+$): IR: 3249, 2974, 2926, 1872, 1652, 1616, 1510, 1488, 1223, 1159, 1090, 1072, 1011, 135, 802 $cm^{-1}$.

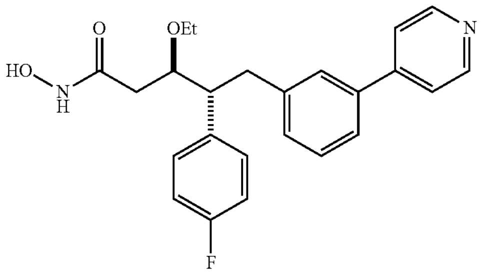 [SMILES: CCO[C@H](CC(=O)NO)[C@H](Cc1cccc(-c2ccncc2)c1)c1ccc(F)cc1]

(3R,4R)-3-ethoxy-4-(4-fluorophenyl)-N-hydroxy-5-(3-(pyridin-4-yl)phenyl)pentanamide (Compound 1-11): MS (API-ES) m/z 409 ($M+H^+$); IR: 3208, 2925, 2853, 1654, 1602, 1511, 1222, 1159, 1094, 832, 790 $cm^{-1}$.

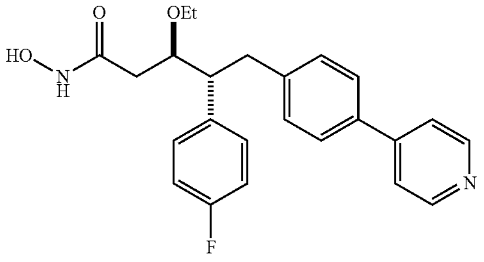 [SMILES: CCO[C@H](CC(=O)NO)[C@H](Cc1ccc(-c2ccncc2)cc1)c1ccc(F)cc1]

(3R,4R)-3-ethoxy-4-(4-fluorophenyl)-N-hydroxy-5-(4-(pyridin-4-yl)phenyl)pentanamide (Compound 1-12): MS (API-ES) m/z 409 ($M+H^+$); IR: 3183, 2974, 1893, 2870, 1654, 1602, 1509, 1222, 1159, 1092, 834, 806, 734 $cm^{-1}$.

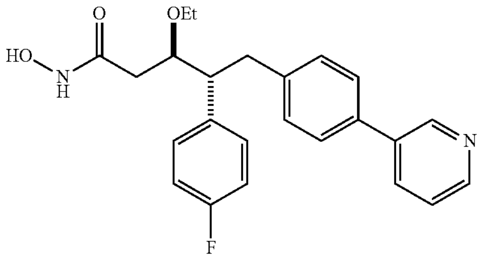 [SMILES: CCO[C@H](CC(=O)NO)[C@H](Cc1ccc(-c2cccnc2)cc1)c1ccc(F)cc1]

(3R,4R)-3-ethoxy-4-(4-fluorophenyl)-N-hydroxy-5-(4-(pyridin-3-yl)phenyl)pentanamide (Compound 1-13): MS (API-ES) m/z 409 (M+H$^+$); IR: 3183, 2974, 1893, 2870, 1654, 1602, 1509, 1222, 1159, 1092, 834, 806, 734 cm$^{-1}$

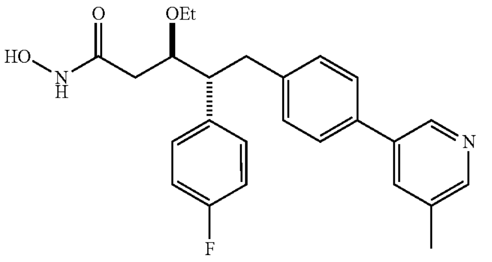 [SMILES: CCO[C@H](CC(=O)NO)[C@H](Cc1ccc(-c2cncc(C)c2)cc1)c1ccc(F)cc1]

(3R,4R)-3-ethoxy-4-(4-fluorophenyl)-N-hydroxy-5-(4-(5-methylpyridin-3-yl)phenyl)pentanamide (Compound 1-14): MS (API-ES) m/z 423 (M+H$^+$); IR: 3182, 2973, 1894, 2871, 1652, 1602, 1509, 1222, 1159, 1092, 834, 807, 734 cm$^{-1}$.

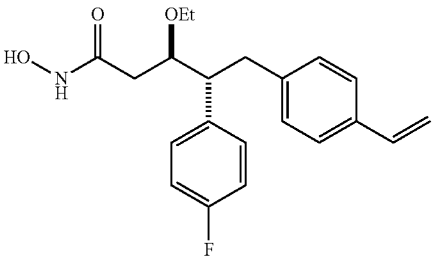 [SMILES: C=Cc1ccc(C[C@H](c2ccc(F)cc2)[C@@H](CC(=O)NO)OCC)cc1]

(3R,4R)-3-ethoxy-4-(4-fluorophenyl)-N-hydroxy-5-(4-vinylphenyl)pentanamide (Compound 1-5): MS (API-ES) m/z 358 (M+H$^+$); IR: 3196, 2977, 2925, 2870, 1652, 1605, 1511, 1442, 1222, 1159, 1091, 1013, 833 cm$^{-1}$.

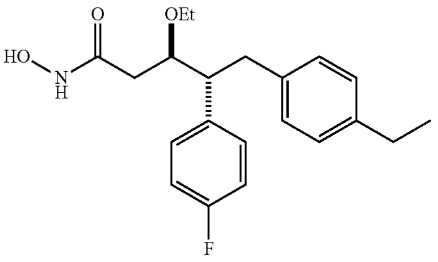 [SMILES: CCO[C@H](CC(=O)NO)[C@H](Cc1ccc(CC)cc1)c1ccc(F)cc1]

(3R,4R)-3-ethoxy-5-(4-ethylphenyl)-4-(4-fluorophenyl)-N-hydroxypentanamide (Compound 1-6): MS (API-ES) m/z 360 (M+H$^+$); IR: 3201, 2968, 2928, 2871, 1652, 1605, 1511, 1451, 1377, 1223, 1159, 1094, 1014, 833 cm$^{-1}$.

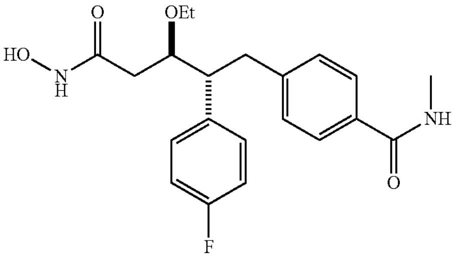 [SMILES: CCO[C@H](CC(=O)NO)[C@H](Cc1ccc(C(=O)NC)cc1)c1ccc(F)cc1]

(4-((2R,3R)-3-ethoxy-2-(4-fluorophenyl)-5-(hydroxyamino)-5-oxopentyl)-N-methylbenzamide (Compound 1-7): LC/MS: $t_R$=4.3 min. MS (API-ES) m/z 389 (M+H$^+$); IR: 3214, 2956, 2924, 2852, 1653, 1647, 1617, 1559, 1506, 1457, 1395, 1261, 1221, 1088, 1021, 836 cm$^{-1}$.

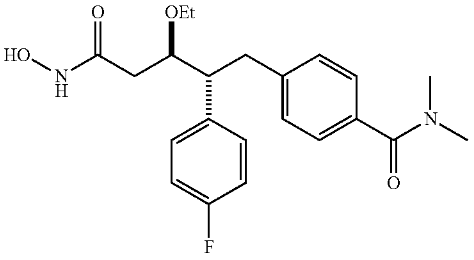 [SMILES: CCO[C@H](CC(=O)NO)[C@H](Cc1ccc(C(=O)N(C)C)cc1)c1ccc(F)cc1]

4-((2R,3R)-3-ethoxy-2-(4-fluorophenyl)-5-(hydroxyamino)-5-oxopentyl)-N,N-dimethylbenzamide (Compound 1-8): MS (API-ES) m/z 403 (M+H$^+$); IR: 3214, 2956, 2923, 2852, 1653, 1647, 1616, 1558, 1539, 1505, 1457, 1380, 1261, 1227, 1155, 1090, 1021 cm$^{-1}$.

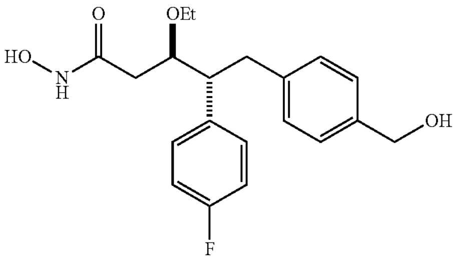 [SMILES: CCO[C@H](CC(=O)NO)[C@H](Cc1ccc(CO)cc1)c1ccc(F)cc1]

(3R,4R)-3-ethoxy-4-(4-fluorophenyl)-N-hydroxy-5-(4-(hydroxymethyl)phenyl)pentanamide (Compound 1-9): MS (API-ES) m/z 362 (M+H$^+$); IR: 3238, 2974, 2925, 2870, 1652, 1538, 1505, 1222, 1159, 1082, 1014, 836, 735 cm$^{-1}$.

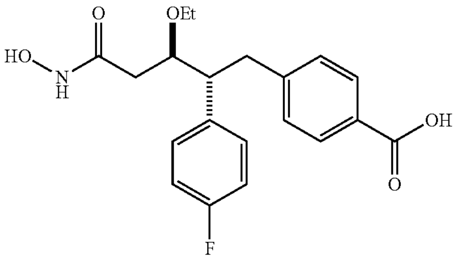 [SMILES: CCO[C@H](CC(=O)NO)[C@H](Cc1ccc(C(=O)O)cc1)c1ccc(F)cc1]

4-((2R,3R)-3-ethoxy-2-(4-fluorophenyl)-5-(hydroxyamino)-5-oxopentyl)benzoic acid (Compound 1-10)

MS (API-ES) m/z 376 (M+H$^+$); IR: 3212, 2953, 2922, 2852, 1694, 1652, 1505, 1220, 1082 cm$^{-1}$.

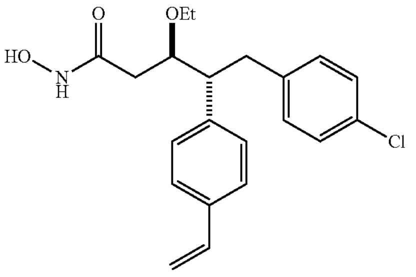 [SMILES: C=Cc1ccc([C@@H](Cc2ccc(Cl)cc2)[C@@H](CC(=O)NO)OCC)cc1]

(3R,4R)-5-(4-chlorophenyl)-3-ethoxy-N-hydroxy-4-(4-vinylphenyl)pentanamide (Compound 3-9): MS (API-ES) m/z 374 ($M+H^+$); IR: 3208, 2976, 2927, 2869, 1652, 1505, 1446, 1407, 1220, 1092, 1021, 840 $cm^{-1}$.

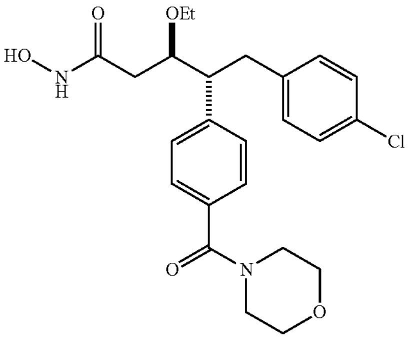 [SMILES: CCO[C@H](CC(=O)NO)[C@H](Cc1ccc(Cl)cc1)c1ccc(C(=O)N2CCOCC2)cc1]

(3R,4R)-5-(4-chlorophenyl)-3-ethoxy-N-hydroxy-4-(4-(morpholine-4-carbonyl)phenyl)pentanamide (Compound 4-5): MS (API-ES) m/z 461 ($M+H^+$); IR: 3208, 2971, 2924, 2856, 1652, 1622, 1492, 1435, 1376, 1278, 1260, 1114, 1091, 1014, 840 $cm^{-1}$

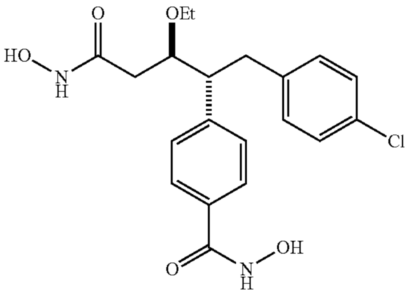 [SMILES: CCO[C@H](CC(=O)NO)[C@H](Cc1ccc(Cl)cc1)c1ccc(C(=O)NO)cc1]

4-((2R,3R)-1-(4-chlorophenyl)-3-ethoxy-5-(hydroxyamino)-5-oxopentan-2-yl)-N-hydroxybenzamide (Compound 4-1): MS (API-ES) m/z 407 ($M+H^+$); IR: 3193, 2926, 2867, 2855, 1694, 1654, 1622, 1470, 1221, 1158, 1098, 1013, 896, 837 $cm^{-1}$.

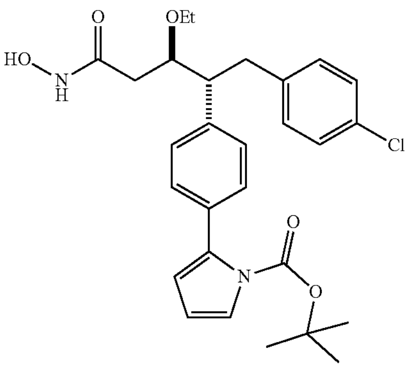 [SMILES: CCO[C@H](CC(=O)NO)[C@H](Cc1ccc(Cl)cc1)c1ccc(-c2cccn2C(=O)OC(C)(C)C)cc1]

tert-butyl 2-(4-((2R,3R)-1-(4-chlorophenyl)-3-ethoxy-5-(hydroxyamino)-5-oxopentan-2-yl)phenyl)-1H-pyrrole-1-carboxylate (Compound 3-24): MS (API-ES) m/z 413 ($M+H^+$-BOC); IR: 3255, 2971, 2926, 2871, 1656, 1645, 1615, 1509, 1492, 1455, 1091, 1014, 837 $cm^{-1}$.

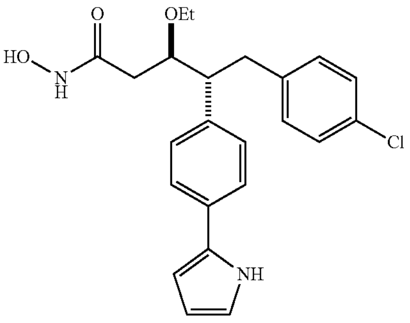 [SMILES: CCO[C@H](CC(=O)NO)[C@H](Cc1ccc(Cl)cc1)c1ccc(-c2ccc[nH]2)cc1]

(3R,4R)-4-(4-(1H-pyrrol-2-yl)phenyl)-5-(4-chlorophenyl)-3-ethoxy-N-hydroxypentanamide (Compound 3-25): MS (API-ES) m/z 413 ($M+H^+$); IR: 3147, 2048, 2970, 1654, 1649, 1631, 1566, 1411, 1091, 1031, 837 $cm^{-1}$.

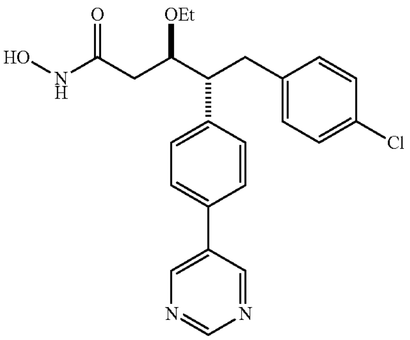 [SMILES: CCO[C@H](CC(=O)NO)[C@H](Cc1ccc(Cl)cc1)c1ccc(-c2cncnc2)cc1]

(3R,4R)-5-(4-chlorophenyl)-3-ethoxy-N-hydroxy-4-(4-(pyrimidin-5-yl)phenyl)pentanamide (Compound 3-26): MS (API-ES) m/z 426 ($M+H^+$): IR: 3343, 3131, 3046, 2972, 2905, 1713, 1652, 1486, 1404, 1328, 1091, 994, 836 $cm^{-1}$

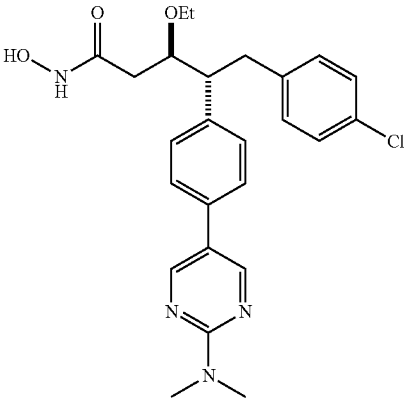 [SMILES: CCO[C@H](CC(=O)NO)[C@H](Cc1ccc(Cl)cc1)c1ccc(-c2cnc(N(C)C)nc2)cc1]

(3R,4R)-5-(4-chlorophenyl)-4-(4-(2-(dimethylamino)pyrimidin-5-yl)phenyl)-3-ethoxy-N-hydroxypentanamide (Compound 3-27): MS (API-ES) m/z 469 ($M+H^+$); IR: 3196, 3030, 2897, 2869, 1652, 1615, 1557, 1505, 1393, 1271, 1236, 1204, 1015, 964, 833 $cm^{-1}$.

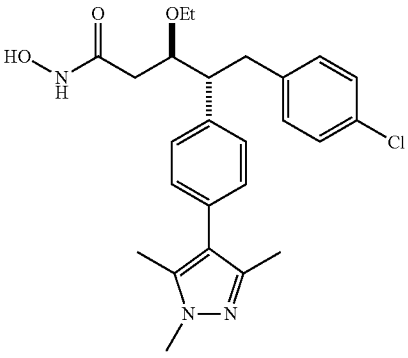 [SMILES: CCO[C@H](CC(=O)NO)[C@H](Cc1ccc(Cl)cc1)c1ccc(-c2c(C)nn(C)c2C)cc1]

(3R,4R)-5-(4-chlorophenyl)-3-ethoxy-N-hydroxy-4-(4-(1,3,5-trimethyl-1H-pyrazol-4-yl)phenyl)pentanamide (Compound 3-28): MS (API-ES) m/z 456 ($M+H^+$); IR: 3185, 2969, 2926, 2862, 1648, 1617, 1560, 1499, 1406, 1300, 1097, 1014, 823 $cm^{-1}$.

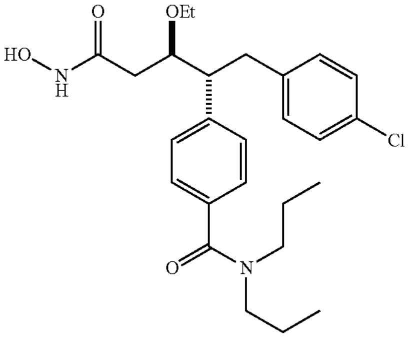 [SMILES: CCCN(CCC)C(=O)c1ccc([C@@H](Cc2ccc(Cl)cc2)[C@@H](CC(=O)NO)OCC)cc1]

4-((2R,3R)-1-(4-chlorophenyl)-3-ethoxy-5-(hydroxyamino)-5-oxopentan-2-yl)-N,N-dipropylbenzamide (Compound 4-2): MS (API-ES) m/z 475 ($M+H^+$); IR: 3205, 2967, 2930, 2875, 1652, 1605, 1464, 1456, 1429, 1373, 1344, 1306, 1258, 1093, 1015, 840 $cm^{-1}$.

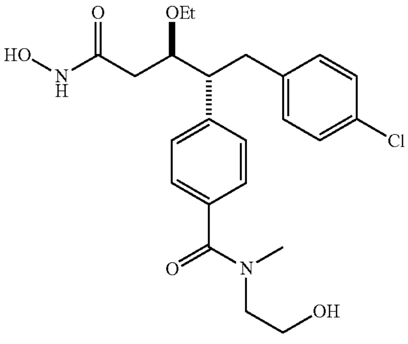 [SMILES: CCO[C@H](CC(=O)NO)[C@H](Cc1ccc(Cl)cc1)c1ccc(C(=O)N(C)CCO)cc1]

4-((2R,3R)-1-(4-chlorophenyl)-3-ethoxy-5-(hydroxyamino)-5-oxopentan-2-yl)-N-(2-hydroxyethyl)-N-methylbenzamide (Compound 4-4): MS (API-ES) m/z 449 ($M+H^+$); IR: 3218, 2973, 2926, 2876, 1652, 1605, 1486, 1407, 1265, 1169, 1086, 1015, 840 $cm^{-1}$

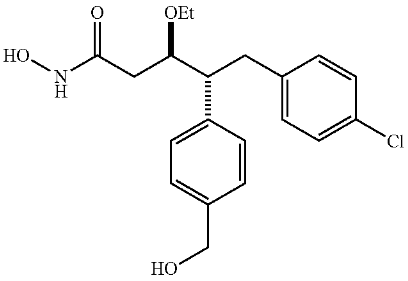 [SMILES: CCO[C@H](CC(=O)NO)[C@H](Cc1ccc(Cl)cc1)c1ccc(CO)cc1]

(3R,4R)-5-(4-chlorophenyl)-3-ethoxy-N-hydroxy-4-(4-(hydroxymethyl)phenyl)pentanamide (Compound 3-10): MS (API-ES) m/z 378 ($M+H^+$): IR: 3212, 2971, 2929, 2863, 1645, 1541, 1501, 1083, 1013 $cm^{-1}$

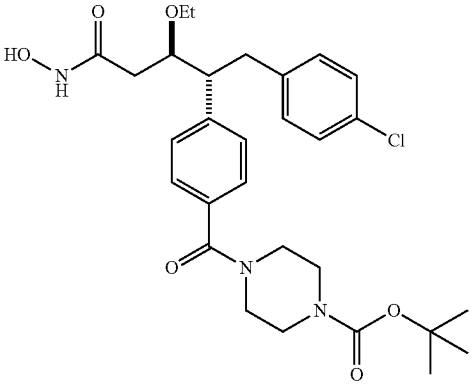 [SMILES: CCO[C@H](CC(=O)NO)[C@H](Cc1ccc(Cl)cc1)c1ccc(C(=O)N2CCN(C(=O)OC(C)(C)C)CC2)cc1]

tert-butyl 4-(4-((2R,3R)-1-(4-chlorophenyl)-3-ethoxy-5-(hydroxyamino)-5-oxopentan-2-yl)benzoyl)piperazine-1-carboxylate (Compound 4-8): MS (API-ES) m/z 560 ($M+H^+$): IR: 3345, 3243, 2975, 2929, 2870, 1668, 1652, 1645, 1557, 1470, 1429, 1370, 1264, 1251, 1202, 1164, 1127, 1091, 1075, 1009, 840 $cm^{-1}$.

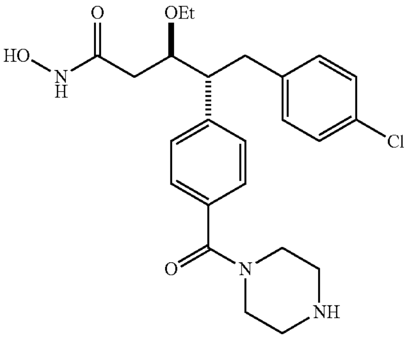 [SMILES: CCO[C@H](CC(=O)NO)[C@H](Cc1ccc(Cl)cc1)c1ccc(C(=O)N2CCNCC2)cc1]

(3R,4R)-5-(4-chlorophenyl)-3-ethoxy-N-hydroxy-4-(4-(piperazine-1-carbonyl)phenyl)pentanamide (Compound 4-9): MS (API-ES) m/z 460 ($M+H^+$); IR: 3395, 3183, 2970, 2926, 2855, 1652, 1622, 1532, 1455, 1290, 1086, 1014, 844 $cm^{-1}$.

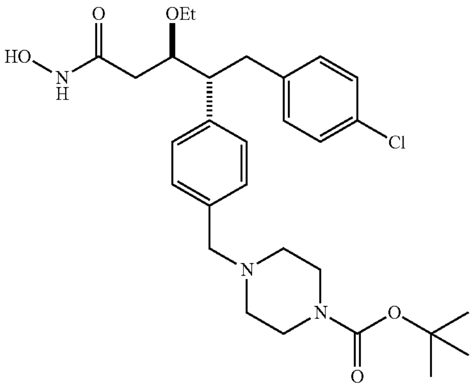 [SMILES: CCO[C@H](CC(=O)NO)[C@H](Cc1ccc(Cl)cc1)c1ccc(CN2CCN(C(=O)OC(C)(C)C)CC2)cc1]

tert-butyl 4-(4-((2R,3R)-1-(4-chlorophenyl)-3-ethoxy-5-(hydroxyamino)-5-oxopentan-2-yl)benzyl)piperazine-1-carboxylate (Compound 3-17): MS (API-ES) m/z 546 (M+H$^+$); IR: 3345, 3253, 2975, 2926, 2870, 2820, 1668, 1661, 1492, 1461, 1422, 1366, 1247, 1168, 1128, 1091, 1003, 864 cm$^{-1}$.

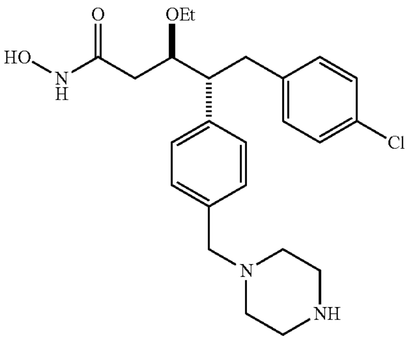 [SMILES: CCO[C@H](CC(=O)NO)[C@H](Cc1ccc(Cl)cc1)c1ccc(CN2CCNCC2)cc1]

(3R,4R)-5-(4-chlorophenyl)-3-ethoxy-N-hydroxy-4-(4-(piperazin-1-ylmethyl)phenyl)pentanamide (Compound 3-18): MS (API-ES) m/z 446 (M+H$^+$); IR: 3387, 3189, 2964, 2926, 2849, 1652, 1634, 1557, 1492, 1445, 1166, 1091, 1014, 943, 854 cm$^{-1}$.

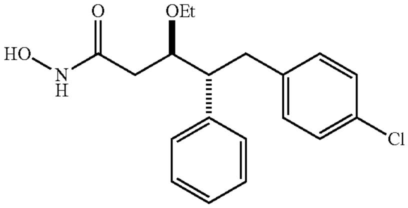 [SMILES: CCO[C@H](CC(=O)NO)[C@H](Cc1ccc(Cl)cc1)c1ccccc1]

(3R,4R)-5-(4-chlorophenyl)-3-ethoxy-N-hydroxy-4-phenylpentanamide (Compound 3-1): MS (API-ES) m/z 348 (M+H$^+$); IR: 3227, 3063, 3029, 2972, 2926, 2898, 1653, 1490, 1091, 1015, 836, 808 cm$^{-1}$.

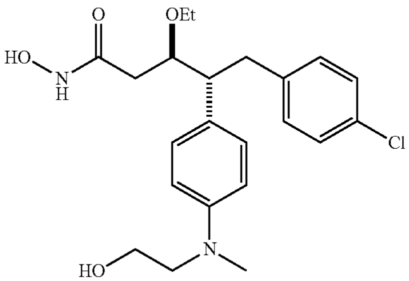 [SMILES: CCO[C@H](CC(=O)NO)[C@H](Cc1ccc(Cl)cc1)c1ccc(N(C)CCO)cc1]

(3R,4R)-5-(4-chlorophenyl)-3-ethoxy-N-hydroxy-4-(4-((2-hydroxyethyl)(methyl)amino)phenyl)pentanamide (Compound 3-21): MS (API-ES) m/z 421 (M+H$^+$); IR: 3220, 2973, 2927, 2884, 1648, 1613, 1518, 1488, 1375, 1350, 1188, 1091, 1014, 818 cm$^{-1}$.

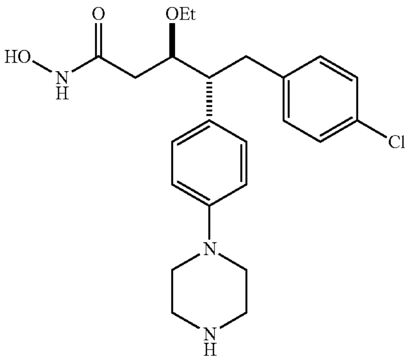 [SMILES: CCO[C@H](CC(=O)NO)[C@H](Cc1ccc(Cl)cc1)c1ccc(N2CCNCC2)cc1]

(3R,4R)-5-(4-chlorophenyl)-3-ethoxy-N-hydroxy-4-(4-(piperazin-1-yl)phenyl)pentanamide (Compound 3-22): MS (API-ES) m/z 432 (M+H$^+$); IR: 2956, 2924, 2854, 1652, 1615, 1557, 1456, 1377, 1234, 1162, 1082 cm$^{-1}$.

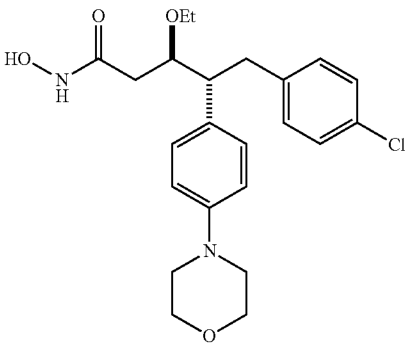 [SMILES: CCO[C@H](CC(=O)NO)[C@H](Cc1ccc(Cl)cc1)c1ccc(N2CCOCC2)cc1]

(3R,4R)-5-(4-chlorophenyl)-3-ethoxy-N-hydroxy-4-(4-morpholinophenyl)pentanamide (Compound 3-23): MS (API-ES) m/z 433 (M+H$^+$); IR: 2956, 2924, 2854, 1652, 1615, 1557, 1456, 1377, 1234, 1162, 1082 cm$^{-1}$.

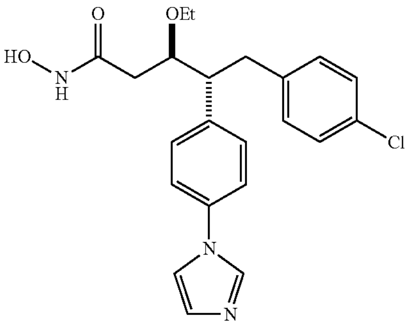 [SMILES: CCO[C@H](CC(=O)NO)[C@H](Cc1ccc(Cl)cc1)c1ccc(-n2ccnc2)cc1]

(3R,4R)-4-(4-(1H-imidazol-1-yl)phenyl)-5-(4-chlorophenyl)-3-ethoxy-N-hydroxypentanamide (Compound 3-29): MS (API-ES) m/z 414 (M+H$^+$): IR: 3176, 2973, 2925, 2896, 2875, 1652, 1524, 1489, 1305, 1247, 1092, 1060, 1014, 964, 833 cm$^{-1}$

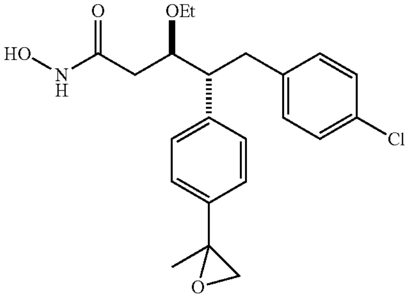 [SMILES: CCO[C@H](CC(=O)NO)[C@H](Cc1ccc(Cl)cc1)c1ccc(C2(C)CO2)cc1]

(3R,4R)-5-(4-chlorophenyl)-3-ethoxy-N-hydroxy-4-(4-(2-methyloxiran-2-yl)phenyl)pentanamide (Compound 3-12): MS (API-ES) m/z 404 (M+H$^+$); IR: 3253, 2972, 2926, 2871, 1652, 1492, 1377, 1244, 1159, 1092, 1043, 1015, 833 cm$^{-1}$.

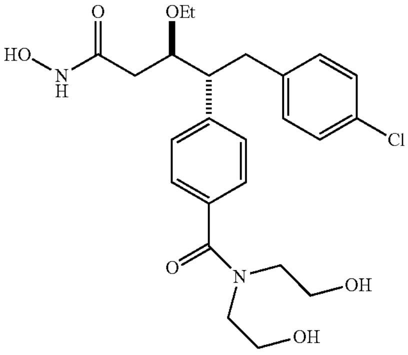 [SMILES: CCO[C@H](CC(=O)NO)[C@H](Cc1ccc(Cl)cc1)c1ccc(C(=O)N(CCO)CCO)cc1]

4-((2R,3R)-1-(4-chlorophenyl)-3-ethoxy-5-(hydroxyamino)-5-oxopentan-2-yl)-N,N-bis(2-hydroxyethyl) benzamide (Compound 4-10): MS (API-ES) m/z 479 (M+H$^+$); IR: 3441, 2956, 2924, 2853, 1646, 1635, 1457, 1075 cm$^{-1}$.

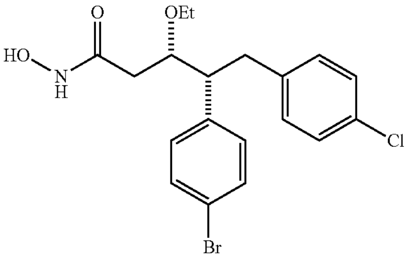 [SMILES: CCO[C@@H](CC(=O)NO)[C@H](Cc1ccc(Cl)cc1)c1ccc(Br)cc1]

(3S,4R)-4-(4-bromophenyl)-5-(4-chlorophenyl)-3-ethoxy-N-hydroxypentanamide (Compound 3-7): MS (API-ES) m/z 426 (M+H$^+$); IR: 3227, 2975, 2926, 2892, 1652, 1492, 1092, 1074, 1010, 822 cm$^{-1}$.

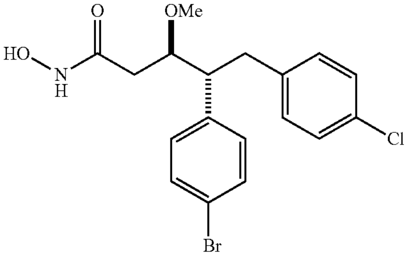 [SMILES: CO[C@H](CC(=O)NO)[C@H](Cc1ccc(Cl)cc1)c1ccc(Br)cc1]

(3R,4R)-4-(4-bromophenyl)-5-(4-chlorophenyl)-N-hydroxy-3-methoxypentanamide (Compound 3-8): MS (API-ES) m/z 411 (M+H$^+$); IR: 3226, 2927, 1652, 1489, 1094, 1074, 1009, 821 cm$^{-1}$.

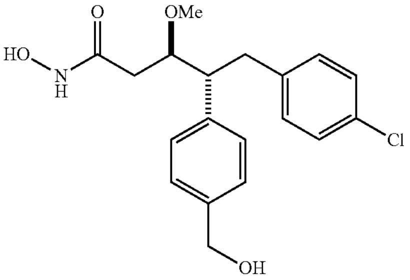 [SMILES: CO[C@H](CC(=O)NO)[C@H](Cc1ccc(Cl)cc1)c1ccc(CO)cc1]

(3R,4R)-5-(4-chlorophenyl)-N-hydroxy-4-(4-(hydroxymethyl)phenyl)-3-methoxypentanamide (Compound 3-11): MS (API-ES) m/z 364 (M+H$^+$); IR: 3227, 2926, 2871, 1652, 1492, 1213, 1179, 1094, 1014, 840 cm$^{-1}$.

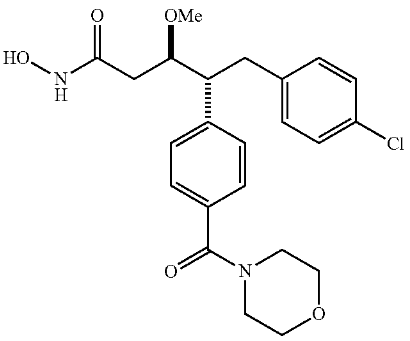

(3R,4R)-5-(4-chlorophenyl)-N-hydroxy-3-methoxy-4-(4-(morpholine-4-carbonyl)phenyl)pentanamide (Compound 4-6): MS (API-ES) m/z 447 (M+H$^+$); IR: 3238, 2926, 2859, 1652, 1622, 1492, 1464, 1436, 1279, 1261, 1112, 1014, 840 cm$^{-1}$.

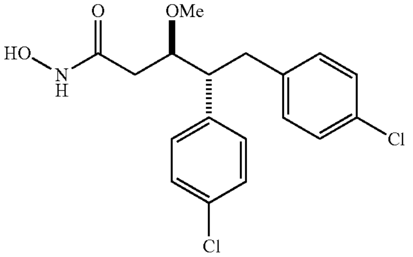 [SMILES: CO[C@H](CC(=O)NO)[C@H](Cc1ccc(Cl)cc1)c1ccc(Cl)cc1]

(3R,4R)-4,5-bis(4-chlorophenyl)-N-hydroxy-3-methoxy-pentanamide (Compound 3-4): MS (API-ES) m/z 368 (M+H$^+$); IR: 3217, 2931, 2835, 1658, 1491, 1408, 1091, 1014, 827 cm$^{-1}$.

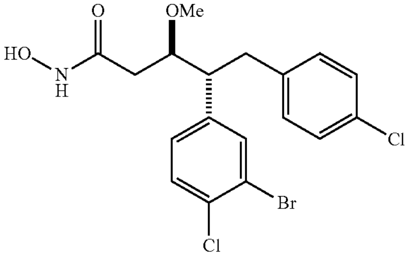 [SMILES: CO[C@H](CC(=O)NO)[C@H](Cc1ccc(Cl)cc1)c1ccc(Cl)c(Br)c1]

(3R,4R)-4-(3-bromo-4-chlorophenyl)-5-(4-chlorophenyl)-N-hydroxy-3-methoxypentanamide (Compound 5-1): MS (API-ES) m/z 445 (M+H$^+$); IR: 3229, 2931, 2833, 1651, 1491, 1466, 1396, 1370, 1264, 1094, 1015, 824 cm$^{-1}$.

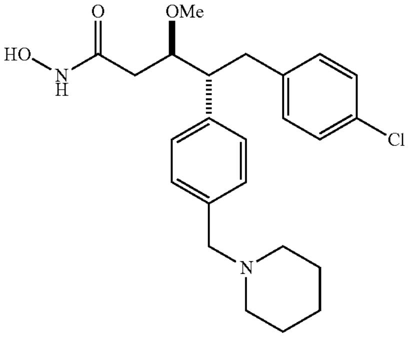 [SMILES: CO[C@H](CC(=O)NO)[C@H](Cc1ccc(Cl)cc1)c1ccc(CN2CCCCC2)cc1]

(3R,4R)-5-(4-chlorophenyl)-N-hydroxy-3-methoxy-4-(4-(piperidin-1-ylmethyl)phenyl)pentanamide (Compound 3-20): MS (API-ES) m/z 431 (M+H$^+$)

IR: 3165, 2955, 2667, 1652, 1428, 1214, 1179, 1095, 854 cm$^{-1}$.

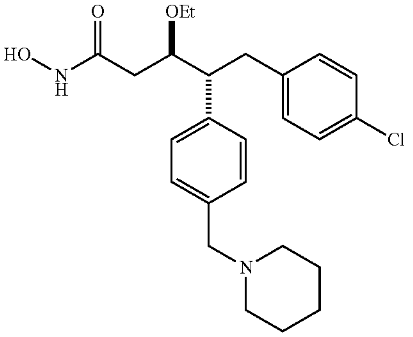 [SMILES: CCO[C@H](CC(=O)NO)[C@H](Cc1ccc(Cl)cc1)c1ccc(CN2CCCCC2)cc1]

(3R,4R)-5-(4-chlorophenyl)-3-ethoxy-N-hydroxy-4-(4-(piperidin-1-ylmethyl)phenyl)pentanamide (Compound 3-19): MS (API-ES) m/z 445 (M+H$^+$); IR: 3179, 2949, 1926, 1649, 1453, 1370, 1090, 853 cm$^{-1}$.

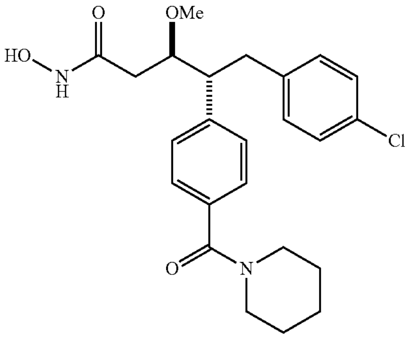 [SMILES: CO[C@H](CC(=O)NO)[C@H](Cc1ccc(Cl)cc1)c1ccc(C(=O)N2CCCCC2)cc1]

(3R,4R)-5-(4-chlorophenyl)-N-hydroxy-3-methoxy-4-(4-(piperidine-1-carbonyl)phenyl)pentanamide (Compound 4-7): MS (API-ES) m/z 445 (M+H$^+$); IR: 3218, 1937, 2857, 1652, 1602, 1492, 1444, 1278, 1099, 1014, 852 cm$^{-1}$.

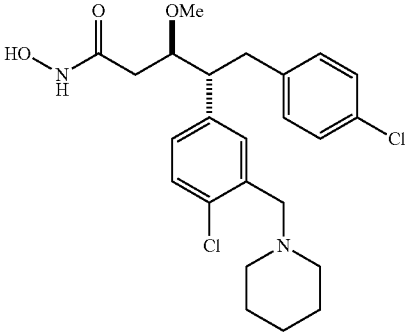 [SMILES: CO[C@H](CC(=O)NO)[C@H](Cc1ccc(Cl)cc1)c1ccc(Cl)c(CN2CCCCC2)c1]

(3R,4R)-4-(4-chloro-3-(piperidin-1-ylmethyl)phenyl)-5-(4-chlorophenyl)-N-hydroxy-3-methoxypentanamide (Compound 5-2): MS (API-ES) m/z 465 (M+H$^+$); IR: 3175, 2926, 2853, 1652, 1489, 1454, 1099, 950, 833 cm$^{-1}$.

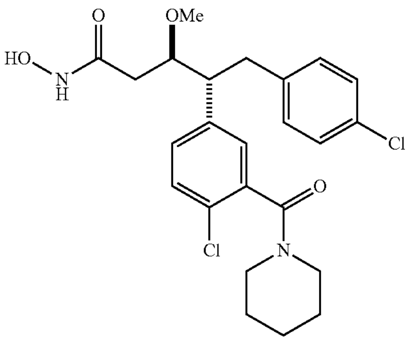 [SMILES: CO[C@H](CC(=O)NO)[C@H](Cc1ccc(Cl)cc1)c1ccc(Cl)c(C(=O)N2CCCCC2)c1]

(3R,4R)-4-(4-chloro-3-(piperidine-1-carbonyl)phenyl)-5-(4-chlorophenyl)-N-hydroxy-3-methoxypentanamide (Compound 5-3): MS (API-ES) m/z 479 (M+H$^+$); IR: 3208, 2939, 2858, 1652, 1608, 1464, 1446, 1289, 1264, 1095 cm$^{-1}$.

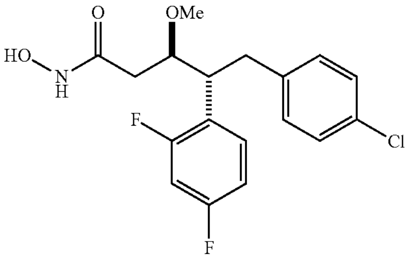 [SMILES: CO[C@H](CC(=O)NO)[C@H](Cc1ccc(Cl)cc1)c1ccc(F)cc1F]

(3R,4R)-5-(4-chlorophenyl)-4-(2,4-difluorophenyl)-N-hydroxy-3-methoxypentanamide (Compound 5-4): MS (API-ES) m/z 370 (M+H$^+$); IR: 3236, 2933, 2837, 1653, 1506, 1491, 1274, 1139, 1091, 1014, 966, 850 cm$^{-1}$.

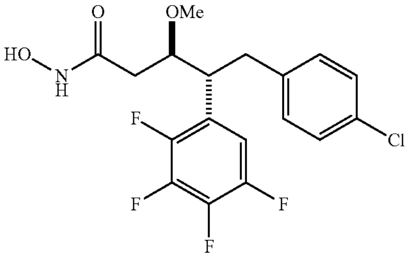 [SMILES: CO[C@H](CC(=O)NO)[C@H](Cc1ccc(Cl)cc1)c1cc(F)c(F)c(F)c1F]

(3R,4R)-5-(4-chlorophenyl)-N-hydroxy-3-methoxy-4-(2,3,4,5-tetrafluorophenyl)pentanamide (Compound 5-6): MS (API-ES) m/z 406 (M+H$^+$); IR: 3238, 2937, 2837, 1650, 1521, 1485, 1363, 1095, 1016 cm$^{-1}$.

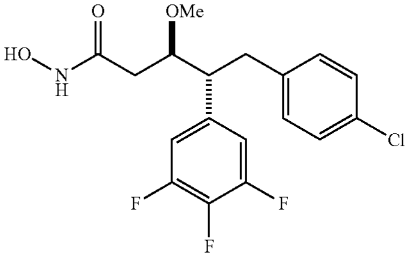 [SMILES: CO[C@H](CC(=O)NO)[C@H](Cc1ccc(Cl)cc1)c1cc(F)c(F)c(F)c1]

(3R,4R)-5-(4-chlorophenyl)-N-hydroxy-3-methoxy-4-(3,4,5-trifluorophenyl)pentanamide (Compound 5-5): MS (API-ES) m/z 388 (M+H$^+$); IR: 3230, 2935, 2839, 1658, 1622, 1529, 1448, 1352, 1236, 1095, 1039, 1014, 858, 806 cm$^{-1}$.

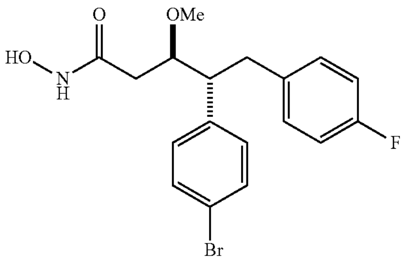 [SMILES: CO[C@H](CC(=O)NO)[C@H](Cc1ccc(F)cc1)c1ccc(Br)cc1]

(3R,4R)-4-(4-bromophenyl)-5-(4-fluorophenyl)-N-hydroxy-3-methoxypentanamide (Compound 1-3): MS (API-ES) m/z 396 (M+H$^+$); IR: 3252, 3041, 2933, 1653, 1506, 1489, 1220, 1157, 1093, 1074, 1010, 823 cm$^{-1}$.

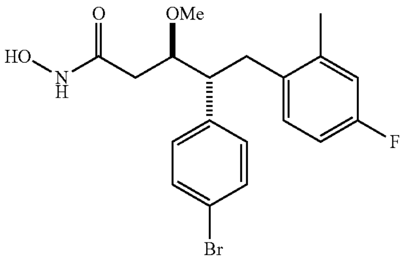 [SMILES: CO[C@H](CC(=O)NO)[C@H](Cc1ccc(F)cc1C)c1ccc(Br)cc1]

(3R,4R)-4-(4-bromophenyl)-5-(4-fluoro-2-methylphenyl)-N-hydroxy-3-methoxypentanamide (Compound 2-1): MS (API-ES) m/z 410 (M+H$^+$); IR: 3227, 2929, 2835, 1645, 1504, 1489, 1249, 1213, 1101, 1074, 1010, 821 cm$^{-1}$.

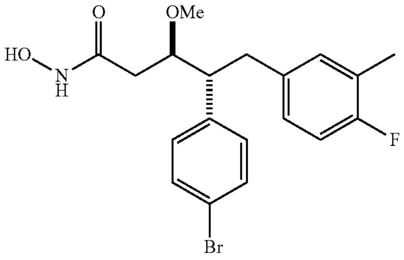 [SMILES: CO[C@H](CC(=O)NO)[C@H](Cc1ccc(F)c(C)c1)c1ccc(Br)cc1]

(3R,4R)-4-(4-bromophenyl)-5-(4-fluoro-3-methylphenyl)-N-hydroxy-3-methoxypentanamide (Compound 2-2): MS (API-ES) m/z 410 (M+H$^+$); IR: 3225, 2933, 1651, 1494, 1265, 1249, 1186, 1151, 1093, 1074, 1010, 958, 819 cm$^{-1}$.

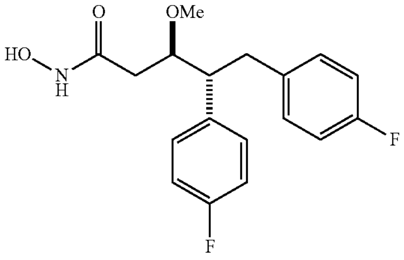 [SMILES: CO[C@H](CC(=O)NO)[C@H](Cc1ccc(F)cc1)c1ccc(F)cc1]

(3R,4R)-5-(4-chlorophenyl)-4-(4-fluorophenyl)-N-hydroxy-3-methoxypentanamide (Compound 3-5): MS (API-ES) m/z 352 (M+H$^+$); IR: 3252, 2933, 2835, 1658, 1510, 1492, 1222, 1159, 1095, 1014, 833 cm$^{-1}$.

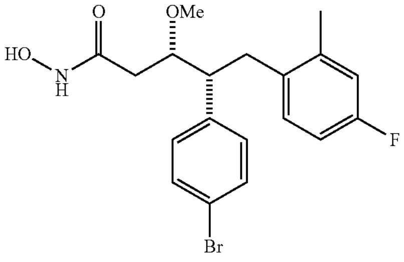 [SMILES: CO[C@@H](CC(=O)NO)[C@H](Cc1ccc(F)cc1C)c1ccc(Br)cc1]

(3S,4R)-4-(4-bromophenyl)-5-(4-fluoro-2-methylphenyl)-N-hydroxy-3-methoxypentanamide (Compound 2-3): MS (API-ES) m/z 410 ($M+H^+$); IR: 3229, 2926, 2834, 1652, 1503, 1486, 1249, 1211, 1104, 1075, 1011, 823 $cm^{-1}$.

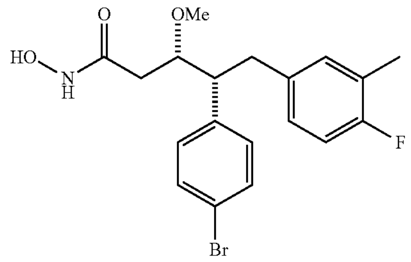 [SMILES: CO[C@@H](CC(=O)NO)[C@H](Cc1ccc(F)c(C)c1)c1ccc(Br)cc1]

(3S,4R)-4-(4-bromophenyl)-5-(4-fluoro-3-methylphenyl)-N-hydroxy-3-methoxypentanamide (Compound 2-4): MS (API-ES) m/z 410 ($M+H^+$); IR: 3228, 2930, 1651, 1450, 1262, 1249, 1186, 1151, 1093, 1074, 1010, 958, 819 $cm^{-1}$.

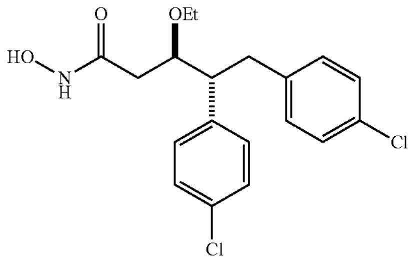 [SMILES: CCO[C@H](CC(=O)NO)[C@H](Cc1ccc(Cl)cc1)c1ccc(Cl)cc1]

(3R,4R)-4,5-bis(4-chlorophenyl)-3-ethoxy-N-hydroxypentanamide (Compound 6-1): MS (API-ES) m/z 382 ($M+H^+$); IR: 3259, 2974, 2926, 1660, 1492, 1091, 1014 $cm^{-1}$.

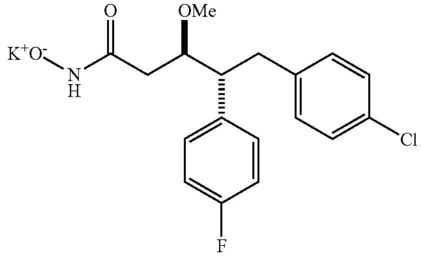

(3R,4R)-5-(4-chlorophenyl)-4-(4-fluorophenyl)-N-hydroxy-3-methoxypentanamide potassium salt (Compound 6-2): MS (API-ES) m/z 352 ($M-K^++2H^+$).

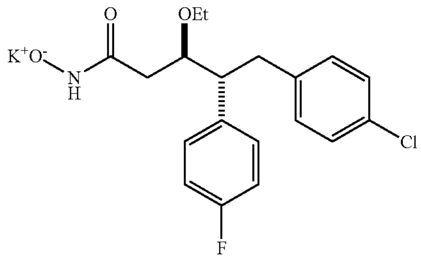

(3R,4R)-5-(4-chlorophenyl)-3-ethoxy-4-(4-fluorophenyl)-N-hydroxypentanamide potassium salt (Compound 6-3): MS (API-ES) m/z 366 ($M-K^++2\ H^+$).

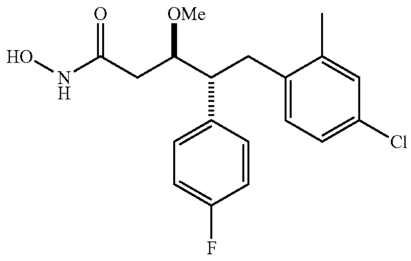 [SMILES: CO[C@H](CC(=O)NO)[C@H](Cc1ccc(Cl)cc1C)c1ccc(F)cc1]

(3R,4R)-5-(4-chloro-2-methylphenyl)-4-(4-fluorophenyl)-N-hydroxy-3-methoxypentanamide (Compound 6-4): MS (API-ES) m/z 366 ($M+H^+$)

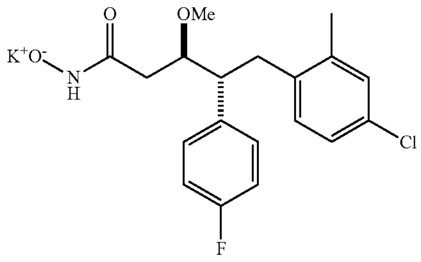

(3R,4R)-5-(4-chloro-2-methylphenyl)-4-(4-fluorophenyl)-N-hydroxy-3-methoxypentanamide potassium salt (Compound 6-5): MS (API-ES) m/z 366 ($M-K^++2\ H^+$)

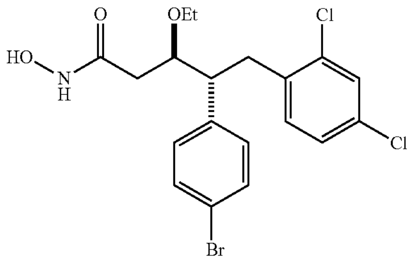 [SMILES: CCO[C@H](CC(=O)NO)[C@H](Cc1ccc(Cl)cc1Cl)c1ccc(Br)cc1]

(3R,4R)-4-(4-bromophenyl)-5-(2,4-dichlorophenyl)-3-ethoxy-N-hydroxypentanamide (Compound 6-6): MS (API-ES) m/z 462 ($M+H^+$)

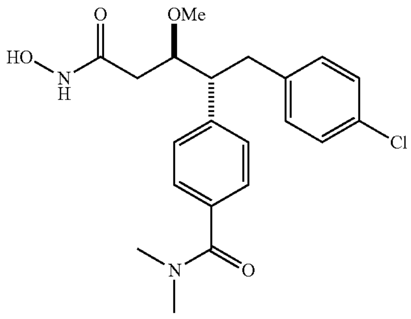 [SMILES: CO[C@H](CC(=O)NO)[C@H](Cc1ccc(Cl)cc1)c1ccc(C(=O)N(C)C)cc1]

4-((2R,3R)-1-(4-chlorophenyl)-5-(hydroxyamino)-3-methoxy-5-oxopentan-2-yl)-N,N-dimethylbenzamide (Compound 6-7): MS (API-ES) m/z 405 (M+H$^+$); IR: 3444, 3211, 2926, 1651, 1614, 1489, 1456, 1408, 1265, 1087, 1014 cm$^{-1}$.

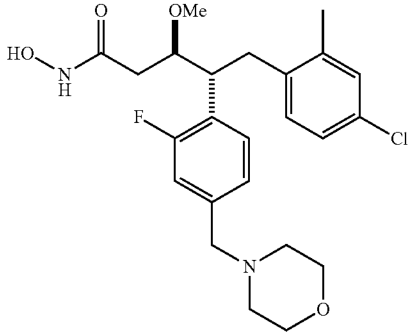 [SMILES: CO[C@H](CC(=O)NO)[C@H](Cc1ccc(Cl)cc1C)c1ccc(CN2CCOCC2)cc1F]

(3R,4R)-5-(4-chloro-2-methylphenyl)-4-(2-fluoro-4-(morpholinomethyl)phenyl)-N-hydroxy-3-methoxypentanamide (Compound 6-8): MS (API-ES) m/z 465 (M+H$^+$); IR: 3404, 3209, 2955, 2928, 2870, 1653, 1541, 1506, 1456, 1435, 1261, 1124, 1101, 1080, 966 cm$^{-1}$.

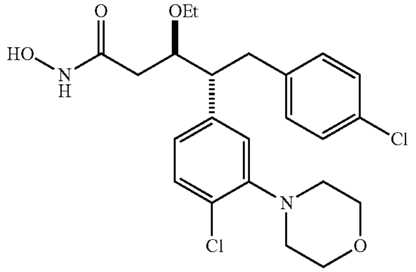 [SMILES: CCO[C@H](CC(=O)NO)[C@H](Cc1ccc(Cl)cc1)c1ccc(Cl)c(N2CCOCC2)c1]

(3R,4R)-4-(4-chloro-3-morpholinophenyl)-5-(4-chlorophenyl)-3-ethoxy-N-hydroxypentanamide (Compound 6-9): MS (API-ES) m/z 467 (M+H$^+$).

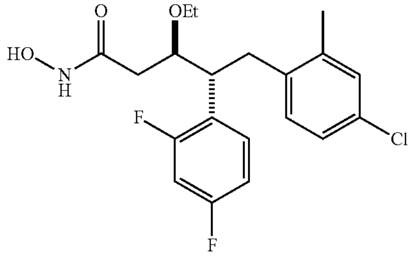 [SMILES: CCO[C@H](CC(=O)NO)[C@H](Cc1ccc(Cl)cc1C)c1ccc(F)cc1F]

(3R,4R)-5-(4-chloro-2-methylphenyl)-4-(2,4-difluorophenyl)-3-ethoxy-N-hydroxypentanamide (Compound 6-10): MS (API-ES) m/z 389 (M+H$^+$); IR: 3230, 2974, 2926, 1651, 1620, 1599, 1504, 1427, 1267, 1139, 1091, 966, 850 cm$^{-1}$.

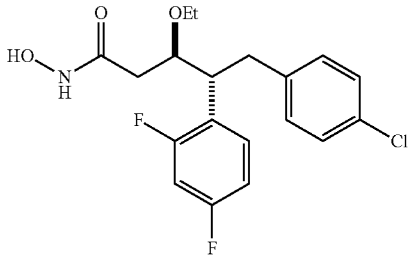 [SMILES: CCO[C@H](CC(=O)NO)[C@H](Cc1ccc(Cl)cc1)c1ccc(F)cc1F]

(3R,4R)-5-(4-chlorophenyl)-4-(2,4-difluorophenyl)-3-ethoxy-N-hydroxypentanamide (Compound 6-11): MS (API-ES) m/z 384 (M+H$^+$); IR: 3236, 2976, 2929, 2897, 1651, 1504, 1427, 1276, 1139, 1091, 1014, 966 cm$^{-1}$.

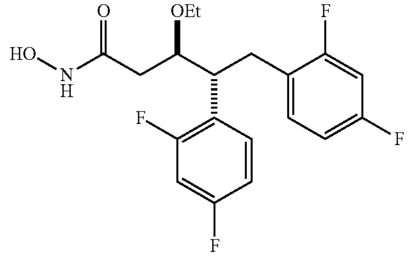 [SMILES: CCO[C@H](CC(=O)NO)[C@H](Cc1ccc(F)cc1F)c1ccc(F)cc1F]

(3R,4R)-4,5-bis(2,4-difluorophenyl)-N-hydroxy-3-methoxypentanamide (Compound 6-12): MS (API-ES) m/z 372 (M+H$^+$).

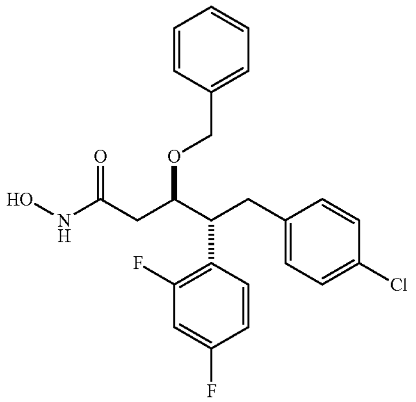 [SMILES: O=C(C[C@@H](OCc1ccccc1)[C@H](Cc1ccc(Cl)cc1)c1ccc(F)cc1F)NO]

(3R,4R)-3-(benzyloxy)-5-(4-chlorophenyl)-4-(2,4-difluorophenyl)-N-hydroxypentanamide (Compound 6-13): MS (API-ES) m/z 446 (M+H$^+$)

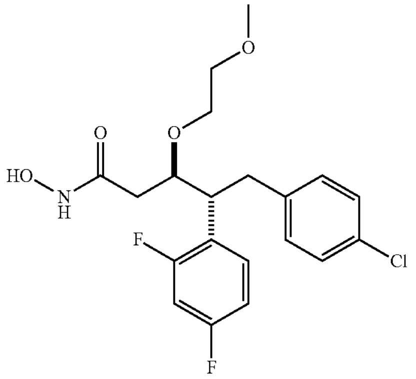 [SMILES: COCCO[C@H](CC(=O)NO)[C@H](Cc1ccc(Cl)cc1)c1ccc(F)cc1F]

(3R,4R)-5-(4-chlorophenyl)-4-(2,4-difluorophenyl)-N-hydroxy-3-(2-methoxyethoxy)pentanamide (Compound 6-14): MS (API-ES) m/z 414 (M+H$^+$)

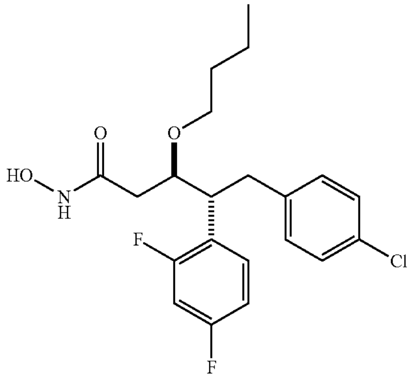 [SMILES: CCCCO[C@H](CC(=O)NO)[C@H](Cc1ccc(Cl)cc1)c1ccc(F)cc1F]

(3R,4R)-3-butoxy-5-(4-chlorophenyl)-4-(2,4-difluorophenyl)-N-hydroxypentanamide (Compound 6-15): MS (API-ES) m/z 412 (M+H$^+$)

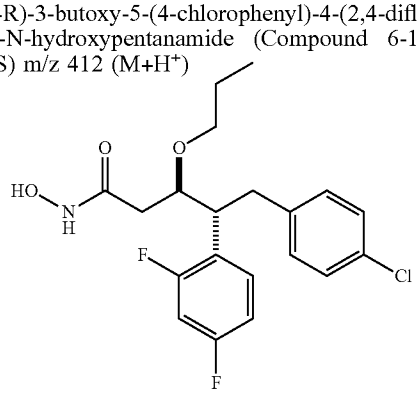

(3R,4R)-5-(4-chlorophenyl)-4-(2,4-difluorophenyl)-N-hydroxy-3-propoxypentanamide (Compound 6-16): MS (API-ES) m/z 398 (M+H$^+$)

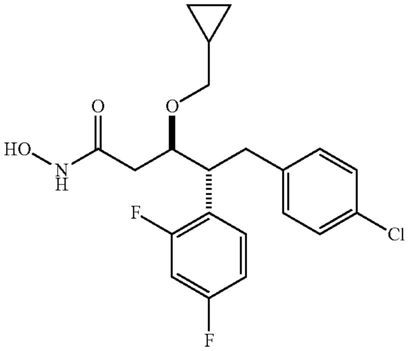

(3R,4R)-5-(4-chlorophenyl)-3-(cyclopropylmethoxy)-4-(2,4-difluorophenyl)-N-hydroxypentanamide (Compound 6-17): MS (API-ES) m/z 410 (M+H$^+$)

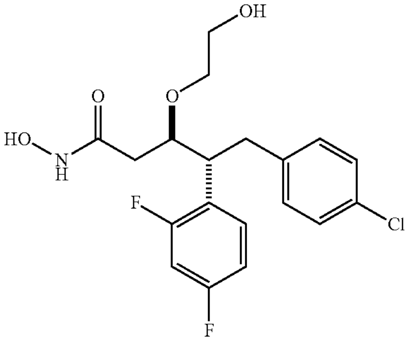

(3R,4R)-5-(4-chlorophenyl)-4-(2,4-difluorophenyl)-N-hydroxy-3-(2-hydroxyethoxy)pentanamide (Compound 6-18): MS (API-ES) m/z 400 (M+H$^+$)

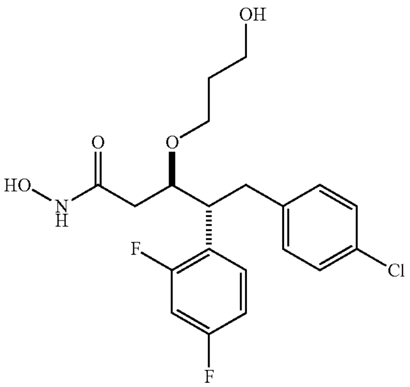

(3R,4R)-5-(4-chlorophenyl)-4-(2,4-difluorophenyl)-N-hydroxy-3-(3-hydroxypropoxy)pentanamide (Compound 6-19): MS (API-ES) m/z 414 (M+H$^+$)

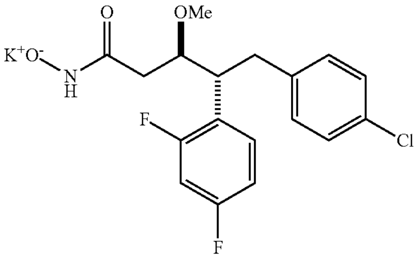

(3R,4R)-5-(4-chlorophenyl)-4-(2,4-difluorophenyl)-N-hydroxy-3-methoxypentanamide potassium salt (Compound 6-20): MS (API-ES) m/z 370 (M-K$^+$+2H$^+$).

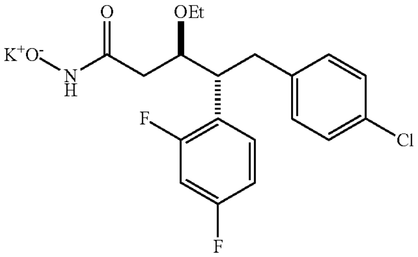

(3R,4R)-5-(4-chlorophenyl)-4-(2,4-difluorophenyl)-3-ethoxy-N-hydroxypentanamide potassium salt (Compound 6-21): MS (API-ES) m/z 384 (M-K$^+$+2H$^+$).

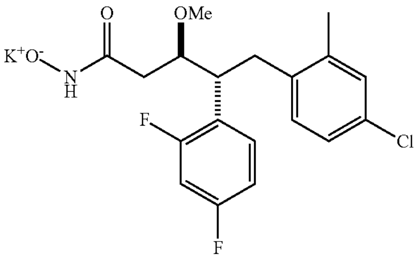

(3R,4R)-5-(4-chloro-2-methylphenyl)-4-(2,4-difluorophenyl)-N-hydroxy-3-methoxypentanamide potassium salt (Compound 6-22): MS (API-ES) m/z 384 (M-K$^+$+2H$^+$).

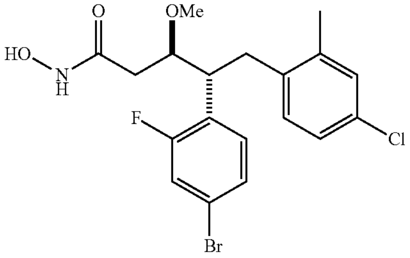

(3R,4R)-4-(4-bromo-2-fluorophenyl)-5-(4-chloro-2-methylphenyl)-N-hydroxy-3-methoxypentanamide (Compound 6-23): MS (API-ES) m/z 444 (M+H$^+$); IR: 3196, 2929, 1651, 1602, 1485, 1406, 1257, 1220, 1103, 1078, 871, 819, 740, 667 cm$^{-1}$.

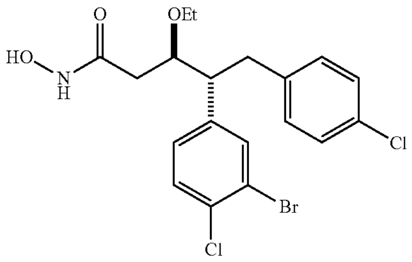

(3R,4R)-4-(3-bromo-4-chlorophenyl)-5-(4-chlorophenyl)-3-ethoxy-N-hydroxypentanamide (Compound 6-24): MS (API-ES) m/z 461 (M+H$^+$); IR: 3255, 2974, 1897, 1653, 1489, 1457, 1398, 1265, 1122, 1091, 1022, 1014, 976 cm$^{-1}$.

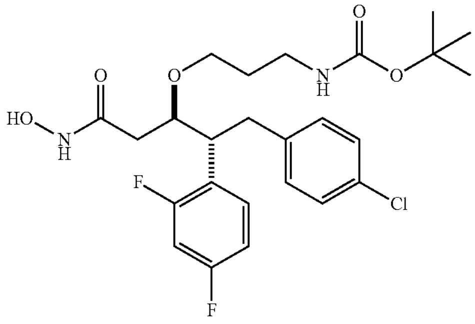

tert-butyl (3-(((3R,4R)-5-(4-chlorophenyl)-4-(2,4-difluorophenyl)-1-(hydroxyamino)-1-oxopentan-3-yl)oxy)propyl) carbamate (Compound 6-25): MS (API-ES) m/z 513 (M+H$^+$).

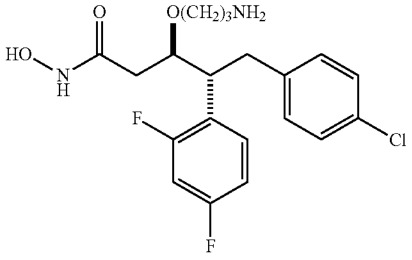

(3R,4R)-3-(3-aminopropoxy)-5-(4-chlorophenyl)-4-(2,4-difluorophenyl)-N-hydroxypentanamide (Compound 6-26): MS (API-ES) m/z 413 (M+H$^+$).

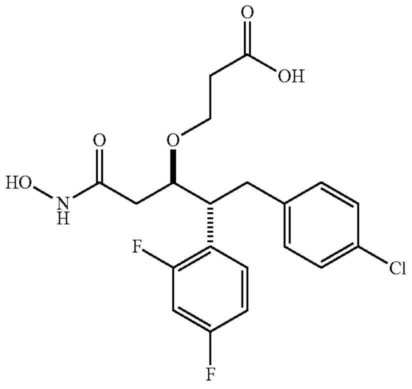

3-(((3R,4R)-5-(4-chlorophenyl)-4-(2,4-difluorophenyl)-1-(hydroxyamino)-1-oxopentan-3-yl)oxy)propanoic acid (Compound 6-27): MS (API-ES) m/z 428 (M+H$^+$)

What is claimed is:

1. A compound of formula I:

I

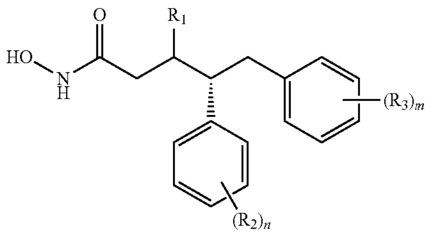

wherein $R_1$ is an alkoxy or $O(CH_2)_pX$;

wherein p is an integer from 2 to 3 and X is OH, $NH_2$, or $CO_2H$;

m is an integer from 0 to 5;

n is an integer from 0 to 5;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen;

each $R_3$ is independently selected from the group consisting of hydrogen, halogen, alkyl, alkenyl, carboxy, hydroxymethyl, amido; and wherein at least one of $R_2$ and $R_3$ is not hydrogen.

2. The compound of claim 1, wherein $R_1$ is an alkoxy in the R-diastereomeric configuration.

3. The compound of claim 1, wherein $R_1$ is an alkoxy in the S-diastereomeric configuration.

4. The compound of claim 1, wherein $R_1$ is ethoxy or methoxy.

5. The compound of claim 1, wherein m=1 and $R_3$ is 4-chloro.

6. The compound of claim 1, wherein m is an integer from 0 to 2.

7. The compound of claim 1, wherein n is an integer from 0 to 4.

8. The compound of claim 1, wherein each $R_2$ is a halogen independently selected from the group consisting of fluorine, bromine, and chlorine.

9. The compound of claim 8, wherein $R_2$ is a 4-substituted halogen.

10. The compound of claim 1, wherein the $R_2$ heterocyclyl or hetereocyclylmethyl group comprises a morpholine, a piperazine, an oxirane, or a piperidine.

11. A compound of formula II:

II

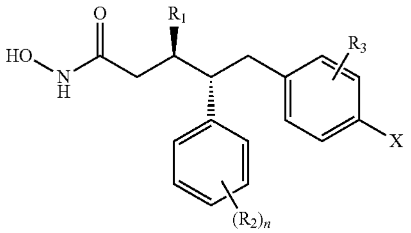

wherein $R_1$ is an alkoxy or $O(CH_2)_pX$;

wherein p is an integer from 2 to 3 and X is OH, $NH_2$, or $CO_2H$;

n is an integer from 0 to 5;

X is a halogen;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen; and $R_3$ is methyl or hydrogen.

12. The compound of claim 11, wherein $R_1$ is methoxy or ethoxy.

13. The compound of claim 11, wherein at least one $R_2$ is halogen.

14. The compound of claim 11, wherein X is chlorine.

15. The compound of claim 11, wherein x is fluorine.

16. The compound of claim 11, wherein at least one $R_2$ is heterocyclyl or hetereocyclylmethyl.

17. The compound of claim 16, wherein the heterocyclyl or hetereocyclylmethyl group comprises a morpholine, a piperazine, an oxirane, or a piperidine.

18. A compound of formula III:

III

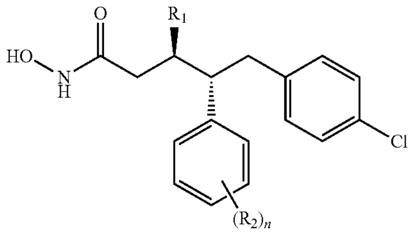

wherein $R_1$ is an alkoxy or $O(CH_2)_pX$;

wherein p is an integer from 2 to 3 and X is OH, $NH_2$, or $CO_2H$;

n is an integer from 0 to 5;

each $R_2$ is independently selected from the group consisting of halogen, hydrogen, alkenyl, hydroxyalkyl, alkoxymethyl, heterocyclyl, hetereocyclylmethyl, amino, amido, hydroxamido, any of which may be optionally substituted with one or more of acyl, alkyl, alkoxy, hydroxyalkyl, or halogen.

19. The compound of claim 11, wherein at least one $R_2$ is halogen.

20. The compound of claim 11, wherein at least one $R_2$ is hydroxymethyl.

21. The compound of claim 11, wherein at least on $R_2$ is heterocyclyl or hetereocyclylmethyl.

22. A pharmaceutical composition comprising a compound according to claim 1 along with a pharmaceutically acceptable carrier.

23. A method of treating *botulinum* toxicity comprising: administering to a subject a pharmaceutical composition comprising a compound according to claim 1.

24. A compound of formula:

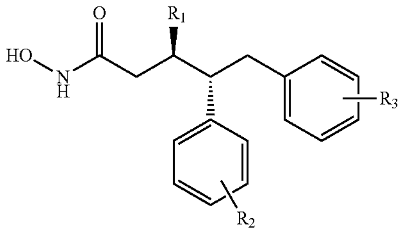

selected from the group consisting of:

$R^1$=OEt, $R^2$=4-F, $R^3$=H;
$R^1$=OEt, $R^2$=4-F, $R^3$=3-Br;
$R^1$=OMe, $R^2$=4-Br, $R^3$=4-F;
$R^1$=OEt, $R^2$=4-F, $R^3$=4-Br;
$R^1$=OEt, $R^2$=4-F, $R^3$=4-CH=$CH_2$;
$R^1$=OEt, $R^2$=4-F, $R^3$=Et;
$R^1$=OEt, $R^2$=4-F, $R^3$=4-C(O)—NHMe;
$R^1$=OEt, $R^2$=4-F, $R^3$=4-C(O)—$NMe_2$;
$R^1$=OEt, $R^2$=4-F, $R^3$=4-$CH_2OH$;
$R^1$=OEt, $R^2$=4-F, $R^3$=4-$CO_2H$;
$R^1$=OEt, $R^2$=4-F, $R^3$=3-(pyridine-4-yl);
$R^1$=OEt, $R^2$=4-F, $R^3$=4-(pyridine-4-yl);
$R^1$=OEt, $R^2$=4-F, $R^3$=4-(pyridine-3-yl); and
$R^1$=OEt, $R^2$=4-F, $R^3$=4-(5-methylpyridine-3-yl).

* * * * *

UNITED STATES PATENT AND TRADEMARK OFFICE

CERTIFICATE OF CORRECTION

PATENT NO. : 9,505,710 B2
APPLICATION NO. : 15/099438
DATED : November 29, 2016
INVENTOR(S) : Alan Thomas Johnson et al.

It is certified that error appears in the above-identified patent and that said Letters Patent is hereby corrected as shown below:

On the Title Page

Column 1, Line 2 in the Abstract [57], "Compounds of formula I are provided: ##STR00001## R.sub.1 is an alkoxy or O(CH.sub.2).sub.pX" should read --Compounds of formula I are provided: ##STR00001## R.sub.1 is an alkoxy or O(CH.sub.2).sub.pX.sup.1--

In the Specification

Column 1, Line 65, "wherein R.sub.1 is an alkoxy or O(CH.sub.2).sub.pX" should read --wherein R.sub.1 is an alkoxy or O(CH.sub.2).sub.pX.sup.1--

Column 2, Line 28, "wherein R.sub.1 is an alkoxy or O(CH.sub.2).sub.pX" should read --wherein R.sub.1 is an alkoxy or O(CH.sub.2).sub.pX.sup.1--

Column 2, Line 56, "wherein R.sub.1 is an alkoxy or O(CH.sub.2).sub.pX" should read --wherein R.sub.1 is an alkoxy or O(CH.sub.2).sub.pX.sup.1--

In the Claims

In Claim 1, Column 51, Line 37, "wherein R.sub.1 is an alkoxy or O(CH.sub.2).sub.pX" should read --wherein R.sub.1 is an alkoxy or O(CH.sub.2).sub.pX.sup.1--

In Claim 11, Column 52, Line 41, "wherein R.sub.1 is an alkoxy or O(CH.sub.2).sub.pX" should read --wherein R.sub.1 is an alkoxy or O(CH.sub.2).sub.pX.sup.1--

In Claim 15, Column 52, Line 61, "The compound of claim 11, wherein x is fluorine" should read --The compound of claim 11, wherein X is fluorin--

In Claim 18, Column 53, Line 15, "wherein R.sub.1 is an alkoxy or O(CH.sub.2).sub.pX" should read --wherein R.sub.1 is an alkoxy or O(CH.sub.2).sub.pX.sup.1--

Signed and Sealed this
Eighth Day of May, 2018

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Enzymatic
      assay
<220> FEATURE:
<221> NAME/KEY: SITE
<222> LOCATION: (1)..(1)
<223> OTHER INFORMATION: Xaa is 2-aminobenzoyl
<220> FEATURE:
<221> NAME/KEY: SITE
<222> LOCATION: (3)..(3)
<223> OTHER INFORMATION: Xaa is D-Arginine
<220> FEATURE:
<221> NAME/KEY: SITE
<222> LOCATION: (14)..(14)
<223> OTHER INFORMATION: Xaa is Norleucine
<220> FEATURE:
<221> NAME/KEY: SITE
<222> LOCATION: (16)..(16)
<223> OTHER INFORMATION: Xaa is 2,4-dinitrophenyl
```

<400> SEQUENCE: 1

```
Xaa Thr Xaa Ile Asp Glu Ala Asn Gln Arg Ala Thr Lys Xaa Lys Xaa
1               5                   10                  15
```

<210> SEQ ID NO 2
<211> LENGTH: 440
<212> TYPE: PRT
<213> ORGANISM: Artificial Sequence
<220> FEATURE:
<223> OTHER INFORMATION: Description of Artificial Sequence: Enzymatic assay

<400> SEQUENCE: 2

```
Met Arg His His His His His His Gly Ala Gln Met Pro Phe Val Asn
1               5                   10                  15

Lys Gln Phe Asn Tyr Lys Asp Pro Val Asn Gly Val Asp Ile Ala Tyr
            20                  25                  30

Ile Lys Ile Pro Asn Ala Gly Gln Met Gln Pro Val Lys Ala Phe Lys
        35                  40                  45

Ile His Asn Lys Ile Trp Val Ile Pro Glu Arg Asp Thr Phe Thr Asn
    50                  55                  60

Pro Glu Glu Gly Asp Leu Asn Pro Pro Pro Glu Ala Lys Gln Val Pro
65                  70                  75                  80

Val Ser Tyr Tyr Asp Ser Thr Tyr Leu Ser Thr Asp Asn Glu Lys Asp
                85                  90                  95

Asn Tyr Leu Lys Gly Val Thr Lys Leu Phe Glu Arg Ile Tyr Ser Thr
            100                 105                 110

Asp Leu Gly Arg Met Leu Leu Thr Ser Ile Val Arg Gly Ile Pro Phe
        115                 120                 125

Trp Gly Gly Ser Thr Ile Asp Thr Glu Leu Lys Val Ile Asp Thr Asn
    130                 135                 140

Cys Ile Asn Val Ile Gln Pro Asp Gly Ser Tyr Arg Ser Glu Glu Leu
145                 150                 155                 160

Asn Leu Val Ile Ile Gly Pro Ser Ala Asp Ile Ile Gln Phe Glu Cys
                165                 170                 175

Lys Ser Phe Gly His Glu Val Leu Asn Leu Thr Arg Asn Gly Tyr Gly
            180                 185                 190

Ser Thr Gln Tyr Ile Arg Phe Ser Pro Asp Phe Thr Phe Gly Phe Glu
        195                 200                 205

Glu Ser Leu Glu Val Asp Thr Asn Pro Leu Leu Gly Ala Gly Lys Phe
    210                 215                 220

Ala Thr Asp Pro Ala Val Thr Leu Ala His Glu Leu Ile His Ala Gly
225                 230                 235                 240

His Arg Leu Tyr Gly Ile Ala Ile Asn Pro Asn Arg Val Phe Lys Val
                245                 250                 255

Asn Thr Asn Ala Tyr Tyr Glu Met Ser Gly Leu Glu Val Ser Phe Glu
            260                 265                 270

Glu Leu Arg Thr Phe Gly Gly His Asp Ala Lys Phe Ile Asp Ser Leu
        275                 280                 285

Gln Glu Asn Glu Phe Arg Leu Tyr Tyr Tyr Asn Lys Phe Lys Asp Ile
    290                 295                 300

Ala Ser Thr Leu Asn Lys Ala Lys Ser Ile Val Gly Thr Thr Ala Ser
305                 310                 315                 320

Leu Gln Tyr Met Lys Asn Val Phe Lys Glu Lys Tyr Leu Leu Ser Glu
                325                 330                 335
```

-continued

```
Asp Thr Ser Gly Lys Phe Ser Val Asp Lys Leu Lys Phe Asp Lys Leu
            340                 345                 350

Tyr Lys Met Leu Thr Glu Ile Tyr Thr Glu Asp Asn Phe Val Lys Phe
        355                 360                 365

Phe Lys Val Leu Asn Arg Lys Thr Tyr Leu Asn Phe Asp Lys Ala Val
    370                 375                 380

Phe Lys Ile Asn Ile Val Pro Lys Val Asn Tyr Thr Ile Tyr Asp Gly
385                 390                 395                 400

Phe Asn Leu Arg Asn Thr Asn Leu Ala Ala Asn Phe Asn Gly Gln Asn
                405                 410                 415

Thr Glu Ile Asn Asn Met Asn Phe Thr Lys Leu Lys Asn Phe Thr Gly
            420                 425                 430

Leu Phe Glu Phe Tyr Lys Leu Leu
        435                 440
```